US012788308B2

(12) United States Patent
Osorio

(10) Patent No.: US 12,788,308 B2
(45) **Date of Patent: *Nov. 10, 2026**

(54) DETECTING, QUANTIFYING, AND/OR CLASSIFYING SEIZURES USING MULTIMODAL DATA

(71) Applicant: Flint Hills Scientific, L.L.C., Lawrence, KS (US)

(72) Inventor: Ivan Osorio, Leawood, KS (US)

(73) Assignee: Flint Hills Scientific, LLC, Lawrence, KS (US)

( * ) Notice: Subject to any disclaimer, the term of this patent is extended or adjusted under 35 U.S.C. 154(b) by 27 days.

This patent is subject to a terminal disclaimer.

(21) Appl. No.: 18/372,272

(22) Filed: Sep. 25, 2023

(65) Prior Publication Data

US 2024/0074693 A1 Mar. 7, 2024

Related U.S. Application Data

(63) Continuation of application No. 17/307,081, filed on May 4, 2021, now Pat. No. 11,801,007, which is a (Continued)

(51) Int. Cl.
*A61B 5/00* (2006.01)
*A61B 5/0205* (2006.01)
(Continued)

(52) U.S. Cl.
CPC .......... *A61B 5/4094* (2013.01); *A61B 5/0205* (2013.01); *A61B 5/02055* (2013.01);
(Continued)

(58) Field of Classification Search
CPC ... A61B 5/4094; A61B 5/02055; A61B 5/746; A61B 5/0402; A61B 5/0816; A61B 5/113; A61B 5/0205; A61B 5/1117; A61B 5/7264; A61B 5/026; A61B 5/021; A61B 5/02405; A61B 5/0488; A61B 5/0531; A61B 5/4266; A61B 7/04; A61B 8/0883; A61B 2562/0219; A61B 5/0245;
(Continued)

(56) References Cited

U.S. PATENT DOCUMENTS 8,641,646 B2 * 2/2014 Colborn ................ G16H 40/63
600/595

FOREIGN PATENT DOCUMENTS

WO WO 2003/001996 * 1/2003 ............... A61B 5/00

* cited by examiner

*Primary Examiner* — Brian T Gedeon
(74) *Attorney, Agent, or Firm* — CF3; Stephen Eisenmann

(57) ABSTRACT

A method, comprising receiving at least one of a signal relating to a first cardiac activity and a signal relating to a first body movement from a patient; triggering at least one of a test of the patient's responsiveness, awareness, a second cardiac activity, a second body movement, a spectral analysis test of the second cardiac activity, and a spectral analysis test of the second body movement, based on at least one of the signal relating to the first cardiac activity and the signal relating to the first body movement; determining an occurrence of an epileptic event based at least in part on said one or more triggered tests; and performing a further action in response to said determination of said occurrence of said epileptic event. Further methods allow classification of epileptic events. Apparatus and systems capable of implementing the method.

12 Claims, 14 Drawing Sheets

Related U.S. Application Data continuation of application No. 16/524,702, filed on Jul. 29, 2019, now Pat. No. 11,006,890, which is a continuation of application No. 15/387,417, filed on Dec. 21, 2016, now Pat. No. 10,405,792, which is a continuation of application No. 14/887,617, filed on Oct. 20, 2015, now Pat. No. 9,545,226, which is a continuation of application No. 14/483,979, filed on Sep. 11, 2014, now Pat. No. 9,186,106, which is a continuation of application No. 13/776,176, filed on Feb. 25, 2013, now Pat. No. 8,852,100, which is a continuation of application No. 13/098,262, filed on Apr. 29, 2011, now Pat. No. 8,382,667, which is a continuation-in-part of application No. 12/896,525, filed on Oct. 1, 2010, now Pat. No. 8,337,404.

(51) Int. Cl.

*A61B 5/08* (2006.01)
*A61B 5/11* (2006.01)
*A61B 5/113* (2006.01)
*A61B 5/33* (2021.01)
*A61N 1/36* (2006.01)
*A61B 5/021* (2006.01)
*A61B 5/024* (2006.01)
*A61B 5/0245* (2006.01)
*A61B 5/026* (2006.01)
*A61B 5/0531* (2021.01)
*A61B 7/04* (2006.01)
*A61B 8/08* (2006.01)
*A61N 1/365* (2006.01)

(52) U.S. Cl.

CPC .......... *A61B 5/0816* (2013.01); *A61B 5/1117* (2013.01); *A61B 5/113* (2013.01); *A61B 5/33* (2021.01); *A61B 5/7264* (2013.01); *A61B 5/746* (2013.01); *A61N 1/36064* (2013.01); *A61N 1/36139* (2013.01); *A61B 5/021* (2013.01); *A61B 5/02405* (2013.01); *A61B 5/0245* (2013.01); *A61B 5/026* (2013.01); *A61B 5/0531* (2013.01); *A61B 5/4266* (2013.01); *A61B 5/686* (2013.01); *A61B 7/04* (2013.01); *A61B 8/0883* (2013.01); *A61B 2562/0219* (2013.01); *A61N 1/36135* (2013.01); *A61N 1/36585* (2013.01)

(58) Field of Classification Search

CPC ............... A61B 5/686; A61N 1/36139; A61N 1/36064; A61N 1/36135; A61N 1/36585; G16H 50/20

See application file for complete search history.

Not to scale

Not to scale

DETECTING, QUANTIFYING, AND/OR CLASSIFYING SEIZURES USING MULTIMODAL DATA

The present application claims priority to and is a Continuation of U.S. patent application Ser. No. 17/307,081, entitled "Detecting, Quantifying, and/or Classifying Seizures Using MultiModal Data", filed May 4, 2021, which claims priority to and is a Continuation of U.S. patent application Ser. No. 16/524,702, entitled "Detecting, Quantifying, and/or Classifying Seizures Using MultiModal Data", filed Jul. 29, 2019 (now U.S. Pat. No. 11,006,890), which claims priority to and is a Continuation of U.S. patent application Ser. No. 15/387,417, entitled "Detecting, Quantifying, and/or Classifying Seizures Using MultiModal Data", filed Dec. 21, 2016 (now U.S. Pat. No. 10,405,792), which is a Continuation of U.S. patent application Ser. No. 14/887,617, entitled "Detecting, Quantifying, and/or Classifying Seizures Using MultiModal Data", filed Oct. 20, 2015 (Now U.S. Pat. No. 9,545,226), which is a Continuation of U.S. patent application Ser. No. 14/483,979, entitled "Detecting, Quantifying, and/or Classifying Seizures Using MultiModal Data", filed Sep. 11, 2014 (Now U.S. Pat. No. 9,186,106) which is a Continuation of U.S. patent application Ser. No. 13/776,176, entitled "Detecting, Quantifying, and/or Classifying Seizures Using MultiModal Data", filed Feb. 25, 2013 (Now U.S. Pat. No. 8,852,100), which is a Continuation of U.S. patent application Ser. No. 13/098,262, entitled "Detecting, Quantifying, and/or Classifying Seizures Using MultiModal Data", filed Apr. 29, 2011 (Now U.S. Pat. No. 8,382,667), which is a Continuation-in-Part of U.S. patent application Ser. No. 12/896,525, entitled "Detecting, Quantifying, and/or Classifying Seizures Using MultiModal Data", filed Oct. 1, 2010 (Now U.S. Pat. No. 8,337,404), where all of these patent applications are incorporated by reference in their entireties.

BACKGROUND OF THE INVENTION

Field of the Invention

This invention relates to medical device systems and methods capable of detecting and, in some embodiments, treating an occurring or impending seizure using multimodal body data.

INCORPORATION BY REFERENCE

The following United States patents or patent applications are incorporated by reference:

- U.S. patent application Ser. No. 12/756,065, filed Apr. 7, 2010.
- U.S. patent application Ser. No. 12/770,562, filed Apr. 29, 2010.
- U.S. patent application Ser. No. 12/884,051, filed Sep. 16, 2010.
- U.S. patent application Ser. No. 12/896,525, filed Oct. 1, 2010.
- U.S. patent application Ser. No. 13/040,996, filed Mar. 4, 2011.

DESCRIPTION OF THE RELATED ART

Of the approximately 60 million people worldwide affected with epilepsy, roughly 23 million people suffer from epilepsy resistant to multiple medications. In the USA alone, the annual cost of epilepsy care is USD 12 billion (in 1995 dollars), most of which is attributable to subjects with pharmaco-resistant seizures. Pharmaco-resistant seizures are associated with an increase mortality and morbidity (e.g., compared to the general population and to epileptics whose seizures are controlled by medications) and with markedly degraded quality of life for patients. Seizures may impair motor control, responsiveness to a wide class of stimuli, and other cognitive functions. The sudden onset of a patient's impairment of motor control, responsiveness, and other cognitive functions precludes the performance of necessary and even simple daily life tasks such as driving a vehicle, cooking, or operating machinery, as well as more complex tasks such as acquiring knowledge and socializing.

Therapies using electrical currents or fields to provide a therapy to a patient (electrotherapy) are beneficial for certain neurological disorders, such as epilepsy. Implantable medical devices have been effectively used to deliver therapeutic electrical stimulation to various portions of the human body (e.g., the vagus nerve) for treating epilepsy. As used herein, "stimulation," "neurostimulation," "stimulation signal," "therapeutic signal," or "neurostimulation signal" refers to the direct or indirect application of an electrical, mechanical, magnetic, electro-magnetic, photonic, acoustic, cognitive, and/or chemical signal to an organ or a neural structure in the patient's body. The signal is an exogenous signal that is distinct from the endogenous electro-chemical activity inherent to the patient's body and also from that found in the environment. In other words, the stimulation signal (whether electrical, mechanical, magnetic, electro-magnetic, photonic, acoustic, cognitive, and/or chemical in nature) applied to a cranial nerve or to other nervous tissue structure in the present invention is a signal applied from a medical device, e.g., a neurostimulator.

A "therapeutic signal" refers to a stimulation signal delivered to a patient's body with the intent of treating a medical condition through a suppressing (e.g., blocking) or modulating effect to neural tissue. The effect of a stimulation signal on neuronal activity may be suppressing or modulating; however, for simplicity, the terms "stimulating", suppressing, and modulating, and variants thereof, are sometimes used interchangeably herein. In general, however, the delivery of an exogenous signal itself refers to "stimulation" of an organ or a neural structure, while the effects of that signal, if any, on the electrical activity of the neural structure are properly referred to as suppression or modulation.

Depending upon myriad factors such as the history (recent and distant) of a patient's brain activity (e.g., electro-chemical, mental, emotional), stimulation parameters and time of day, to name a few, the effects of stimulation upon the neural tissue may be excitatory or inhibitory, facilitatory or disfacilitatory and may suppress, enhance, or leave unaltered neuronal activity. For example, the suppressing effect of a stimulation signal on neural tissue would manifest as the blockage of abnormal activity (e.g., epileptic seizures) see Osorio et al., Ann Neurol 2005; Osorio & Frei IJNS 2009) The mechanisms thorough which this suppressing effect takes place are described in the foregoing articles. Suppression of abnormal neural activity is generally a threshold or suprathreshold process and the temporal scale over which it occurs is usually in the order of tens or hundreds of milliseconds. Modulation of abnormal or undesirable neural activity is typically a "sub-threshold" process in the spatio-temporal domain that may summate and result under certain conditions, in threshold or suprathreshold neural events. The temporal scale of modulation is usually longer than that of suppression, encompassing seconds to hours, even months. In addition to inhibition or dysfacilitation, modification of neural activity (e.g., wave annihilation) may be exerted through collision with identical, similar or dissimilar waves, a concept borrowed from wave mechanics, or through phase resetting (Winfree).

In some cases, electrotherapy may be provided by implanting an electrical device, e.g., an implantable medical device (IMD), inside a patient's body for stimulation of a nervous tissue, such as a cranial nerve. Generally, electrotherapy signals that suppress or modulate neural activity are delivered by the IMD via one or more leads. When applicable, the leads generally terminate at their distal ends in one or more electrodes, and the electrodes, in turn, are coupled to a target tissue in the patient's body. For example, a number of electrodes may be attached to various points of a nerve or other tissue inside a human body for delivery of a neurostimulation signal.

While contingent (also referred to as "closed-loop," "active," or "feedback" stimulation; i.e., electrotherapy applied in response to sensed information, such as heart rate) stimulation schemes have been proposed, non-contingent, programmed periodic stimulation is the prevailing modality. For example, vagus nerve stimulation for the treatment of epilepsy usually involves a series of grouped electrical pulses defined by an "on-time" (such as 30 sec.) and an "off-time" (such as 5 min.). This type of stimulation is also referred to as "open-loop," "passive," or "non-feedback" stimulation. Each sequence of pulses during an on-time may be referred to as a "pulse burst." The burst is followed by the off-time period in which no signals are applied to the nerve. During the on-time, electrical pulses of a defined electrical current (e.g., 0.5-3.5 milliamps) and pulse width (e.g., 0.25-1.0 milliseconds) are delivered at a defined frequency (e.g., 20-30 Hz) for a certain duration (e.g., 10-60 seconds). The on-time and off-time parameters together define a duty cycle, which is the ratio of the on-time to the sum of the on-time and off-time, and which describes the fraction of time that the electrical signal is applied to the nerve.

In VNS, the on-time and off-time may be programmed to define an intermittent pattern in which a repeating series of electrical pulse bursts are generated and applied to a cranial nerve such as the vagus nerve. The off-time is provided to minimize adverse effects and conserve power. If the off-time is set at zero, the electrical signal in conventional VNS may provide continuous stimulation to the vagus nerve. Alternatively, the off time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-300 Hz (i.e., 20 pulses per second to 300 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Although neurostimulation has proven effective in the treatment of a number of medical conditions, it would be desirable to further enhance and optimize neurostimulation-based therapy for this purpose. For example, it may be desirable to detect an occurring or impending seizure. Such detection may be useful in triggering a therapy, monitoring the course of a patient's disease, or the progress of his or her treatment thereof. Alternatively or in addition, such detection may be useful in issuing a warning of an impending or on-going seizure. Such a warning may, for example, minimize the risk of injury or death. Said warning may be perceived by the patient, a physician, a caregiver, or a suitably programmed computer and allow that person or computer program to take action intended to reduce the likelihood, duration, or severity of the seizure or impending seizure, or to facilitate further medical treatment or intervention for the patient. In particular, detection of an occurring or impending seizure enables the use of contingent neurostimulation. The state of the art does not provide an efficient and effective means for performing such detection and/or warning. Conventional VNS stimulation as described above does not detect occurring or impending seizures.

Closed-loop neurostimulation therapies for treating epilepsy have been proposed in which stimulation is triggered based upon factors including EEG activity (see, e.g., U.S. Pat. Nos. 5,995,868 and 7,280,867) as well as cardiac-based activity (see, e.g., U.S. Pat. Nos. 6,961,618 and 5,928,272). EEG- or ECoG-based approaches involving recording of neural electrical activity at any spatio-temporal scale involve determination of one or more parameters from brain electrical activity that indicate a seizure. Such approaches have met with limited success and have a number of drawbacks, including highly invasive and technically demanding and costly surgery for implanted systems. Approaches that do not invade the brain have marked limitations due mainly to the extremely low/unreliable S/N, and poor patient compliance with, e.g., the patient wearing electrodes on the scalp for extended periods.

SUMMARY OF THE INVENTION

In one embodiment, the present invention provides a method. In one embodiment, the method comprises receiving at least one of signal relating to a first cardiac activity from a patient and a signal relating to a first body movement from the patient; deriving at least one patient index from said at least one received signal; triggering at least one of a test of the patient's responsiveness, a test of the patient's awareness, a test of a second cardiac activity of the patient, a test of a second body movement of the patient, a spectral analysis test of a second cardiac activity of the patient, and a spectral analysis test of the second body movement of the patient, based on said at least one patient index; determining an occurrence of an epileptic event based at least in part on the one or more triggered tests; and performing a further action in response to the determination of the occurrence of the epileptic event.

In one embodiment, the present invention provides a method. In one embodiment, the method comprises receiving at least two body signals selected from the group consisting of a signal relating to a first body movement, a signal relating to a first cardiac activity, a responsiveness signal, an awareness signal, a signal relating to a second cardiac activity, a signal relating to a second body movement, a spectral analysis signal relating to the second cardiac activity, and a spectral analysis signal relating to the second body movement; determining an occurrence of a generalized tonic-clonic epileptic seizure, the determination being based upon the correlation of at least two features, at least one feature being of each of the at least two body signals, wherein: the feature of the first cardiac activity signal is an increase in the patient's heart rate above an interictal reference value; the feature of the first body movement signal is at least one of (i) an increase in axial or limb muscle tone substantially above an interictal or exercise value for the patient, (ii) a decrease in axial muscle tone in a non-recumbent patient, below the value associated with a first, non-recumbent position, (iii) fall followed by an increase in body muscle tone, or (iv) a fall followed by generalized body movements; the feature of the responsiveness signal is a decrease in the patient's responsiveness below an interictal reference value; the feature of the awareness signal is a decrease in the patient's awareness below an interictal reference value; the feature of the second cardiac activity signal is a correlation with an ictal cardiac activity reference signal; the feature of the second body movement signal is a correlation with an ictal body movement reference signal; the feature of the spectral analysis signal of the second cardiac activity is a correlation with an ictal cardiac activity spectral analysis reference signal; or the feature of the spectral analysis signal of the second body movement is a correlation with an ictal body movement spectral analysis reference signal; and performing a further action in response to the determination of the occurrence of the epileptic event.

In one embodiment, the present invention provides a method. In one embodiment, the method comprises receiving at least two body signals selected from the group consisting of a signal relating to a first body movement, a signal relating to a first cardiac activity, a responsiveness signal, an awareness signal, a signal relating to a second cardiac activity, a signal relating to a second body movement, a spectral analysis signal relating to the second cardiac activity, and spectral analysis signal relating to the second body movement; and determining an occurrence of a partial epileptic seizure based upon a correlation of two features, at least one feature being of each of the at least two body signals, wherein: the feature of the first cardiac signal is a value outside an interictal reference value range; the feature of the first body movement signal is a body movement associated with a partial seizure; the feature of the second cardiac activity signal is a correlation with an ictal cardiac activity reference signal; the feature of the second body movement signal is a correlation with an ictal body movement reference signal; the feature of the spectral analysis signal of the second cardiac activity is a correlation with an ictal cardiac activity spectral analysis reference signal; or the feature of the spectral analysis signal of the second body movement is a correlation with an ictal body movement spectral analysis reference signal; and performing a further action in response to the determination of the occurrence of the epileptic event.

In other embodiments, a computer readable program storage device is provided that is encoded with instructions that, when executed by a computer, perform a method described above.

In one embodiment, a medical device is provided comprising an autonomic signal module, a kinetic signal module, a detection module, and a processor adapted to perform a method as described above.

BRIEF DESCRIPTION OF THE DRAWINGS

The invention may be understood by reference to the following description taken in conjunction with the accompanying drawings, in which like reference numerals identify like elements, and in which:

FIG. 1A shows an external device in communication with a sensor. FIG. 1B shows an implanted device providing a therapeutic signal to a structure of the patient's body, each in accordance with one illustrative embodiment of the present invention;

Figure 1A:
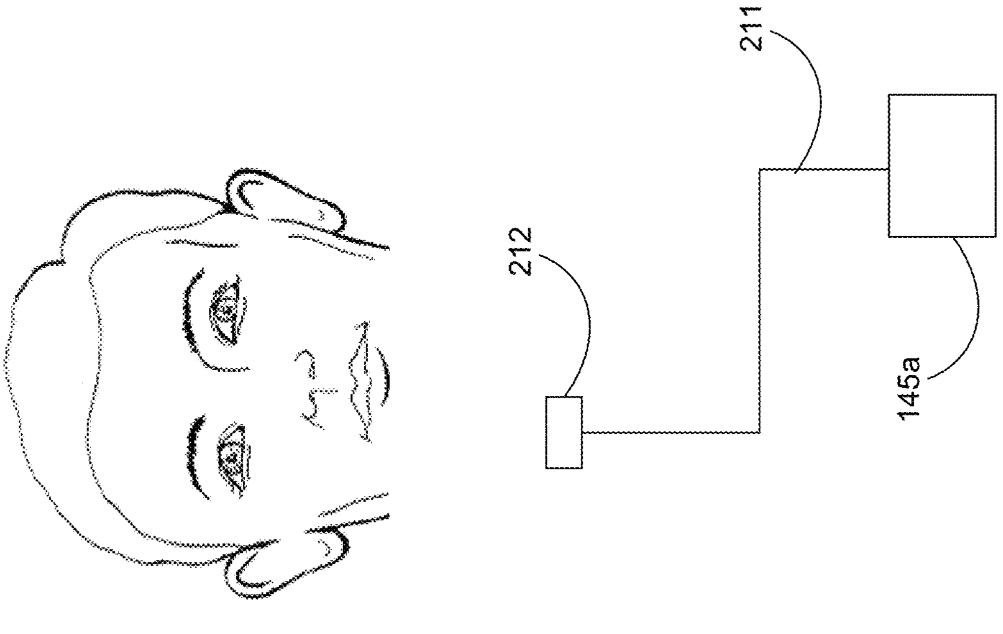
FIGS. 1A-1B provide stylized diagrams of medical devices.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF ILLUSTRATIVE EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering a therapeutic signal generated by an IMD to a tissue), sensing electrodes (i.e., electrodes for sensing a physiological indication of a state of a patient's body), and/or electrodes that are capable of delivering a therapeutic signal, as well as performing a sensing function.

Identification of changes in brain state are generally described in U.S. patent application Ser. No. 12/896,525, filed Oct. 1, 2010, incorporated herein by reference. As stated therein, implanted sensors or electrodes beneath the scalp but above the outer skull table or intra-cranial (epidural, subdural or depth) have been used to overcome the limitations of scalp recordings. However, the quality of data is limited; there are risks (e.g., infection, bleeding, brain damage) associated with these devices; and in addition, at this time, there are at most about 300 neurosurgeons capable of implanting intracranial electrodes, far too few to perform such implantation for the roughly 900,000 pharmaco-resistant epileptics in the United States.

The basis for our work in using multimodal signals for detection of state changes in the brain is as generally described in U.S. patent application Ser. No. 12/896,525, filed Oct. 1, 2010. Various multimodal signals that may be used in the invention are set forth in the following table:

TABLE 1

| Multimodal Signals |
|---|
| **Autonomic** |
| Cardiac: EKG, PKG, Echocardiography, Apexcardiography (ApKG), Intra-cardiac pressure, Cardiac blood flow, cardiac thermography; from which can be derived, e.g., heart rate (HR), change of HR, rate of change of HR, heart rhythm, changes in heart rhythm, heart rate variability (HRV), change of HRV, rate of change of HRV, HRV vs. HR. Also, heart morphology (e.g., size) blood pressure (arterial and venous), heart sounds, , heartbeat wave morphology, heartbeat complex morphology, and magnitude and shape of thoracic wall deflection.<br>Vascular: Arterial Pressure, Arterial and venous blood wave pressure morphology; Arterial and venous blood flow velocity and degree of turbulence, arterial and venous blood flow sounds, arterial and venous temperature<br>Respiratory: Frequency, tidal volume, minute volume, respiratory wave morphology, respiratory sounds, end-tidal CO2, Intercostal EMG, Diaphragmatic EMG, chest wall and abdominal wall motion, from which can be derived, e.g.,, respiration rate (RR), change of RR, rate of change of RR, respiratory rhythm, morphology of breaths. Also, arterial gas concentrations, including oxygen saturation, as well as blood pH can be considered respiratory signals.<br>Dermal: Skin resistance, skin temperature, skin blood flow, sweat gland activity<br>Concentrations of catecholamines (and their metabolites) and acetylcholine or acetylcholinesterase activity in blood, saliva and other body fluids concentrations and its rate of change. |
| **Neurologic** |
| Cognitive/behavioral: Level of consciousness, attention, reaction time, memory, visuospatial, language, reasoning, judgment, mathematical calculations, auditory and/or visual discrimination<br>Kinetic: Direction, speed/acceleration, trajectory (1D to 3D), pattern, and quality of movements, force of contraction, body posture, body orientation/position, body part orientation/position in reference to each other and to imaginary axes, muscle tone, agonist-to-antagonist muscle tone relation, from which can be derived, e.g., information about gait, posture, accessory movements, falls<br>Vocalizations: Formed, unformed<br>EEG/ECoG, Evoked potentials, field potentials, single unit activity<br>Endocrine: Prolactin, luteinizing hormone, follicle stimulation hormone, growth hormone, ACTH, cortisol, vasopressin, beta-endorphin, beta, lipotropin-, corticotropin-releasing factor (CRF)<br>Stress Markers: CK, troponin, reactive oxygen and nitrogen species including but not limited to iso- and neuro-prostanes and nitrite/nitrate ratio, gluthatione, gluthatione disulfide and gluthatione peroxidase activity, citrulline, protein carbonyls, thiobarbituric acid, the heat shock protein family, catecholamines, lactic acid, N-acetylaspartate, and metabolites of any of the foregoing.<br>Metabolic: arterial pH and gases, lactate/pyruvate ratio, electrolytes, glucose |

Terms such as "epileptic event" and "reference value," among others, have been defined in U.S. patent application Ser. No. 12/896,525, filed Oct. 1, 2010. "Interictal" refers to a period after a post-ictal period and before a pre-ictal period.

FIGS. 4-7 have been substantially fully described in U.S. patent application Ser. No. 12/896,525, filed Oct. 1, 2010.

Various features of signals for various types of seizures are also generally described in U.S. patent application Ser. No. 12/896,525, filed Oct. 1, 2010.

U.S. patent application Ser. No. 12/896,525, filed Oct. 1, 2010 also discusses methods capable of distinguishing epileptic generalized from non-epileptic generalized or "convulsive" seizures whose kinetic activity, but not pathophysiology, resembles that of epileptic seizures.

The selectivity (Sl), sensitivity (Se) and specificity (Sp) of various signal features are generally described in U.S. patent application Ser. No. 12/896,525, filed Oct. 1, 2010. U.S. patent application Ser. No. 12/896,525 also discusses consideration of these and other signal features in determining optimal signal(s) for use in detection of epileptic events in a particular patient, of a particular type, or the like.

A Positive Predictive Value (PPV) of a signal or combination of signals is generally described in U.S. patent application Ser. No. 12/896,525, filed Oct. 1, 2010. The person of ordinary skill in the art will also understand a Negative Predictive Value (NPV) of a signal, defined as:

(number of True Negatives)/number of True Negatives+number of False Negatives.

In one embodiment, the present invention relates to a method, comprising receiving at least one of a signal relating to a first cardiac activity from a patient and a signal relating to a first body movement from the patient; deriving at least one patient index from said at least one received signal; triggering at least one of a test of the patient's responsiveness, a test of the patient's awareness, a test of a second cardiac activity of the patient, a test of a second body movement of the patient, a spectral analysis test of a second cardiac activity of the patient, and a spectral analysis test of a second body movement of the patient, based on said at least one patient index; determining an occurrence of an epileptic event based at least in part on the one or more triggered tests; and performing a further action in response to the determination of the occurrence of the epileptic event.

Cardiac activity signals, as well as techniques for determining them, are generally described in U.S. patent application Ser. No. 12/896,525, filed Oct. 1, 2010.

Body movement (a.k.a. kinetic) signals, as well as techniques for determining them, are generally described in U.S. patent application Ser. No. 12/896,525, filed Oct. 1, 2010. It should be borne in mind that the terms "body movement" and "kinetic," as used herein, also encompass the absence of specific body movements (motionless).

The term, and concept of, "responsiveness" as used in reference to the embodiments described herein, has a motor and a cognitive component which may be strongly correlated or dissociated; further the motor component may be in the form of a simple response (e.g., withdrawal of a limb from a pain source) or complex (e.g. drawing a triangle in response to a command). Consequently, responsiveness may be tested using simple stimuli (e.g., acoustic in the form of a loud noise or sensory in the form of a pinprick) or complex (e.g., complex reaction time tests; questions probing knowledge, judgment, abstraction, memory, etc.). In this invention, when "responsiveness" is tested using complex stimuli, "awareness" is being probed and therefore in that case these terms/concepts are used interchangeably. The meaning of "responsiveness" is thus, context dependent: if the objective is to determine if a patient generates simple motor responses or movements, the term "responsiveness" may be used and if it is to test the presence and quality of complex responses, "awareness" may replace responsiveness.

As used herein, "spectral analysis" encompasses spectral analyses using at least one of the known methods (e.g., Fourier-based, wavelet based; multifractal spectral, etc) of cardiac activity or body movements. Spectral analysis techniques are known to the person of ordinary skill in the art and can be implemented by such a person having the benefit of the present disclosure. Spectral analysis may be discrete or continuous. Spectral analysis of a cardiac activity can comprise spectral analysis of heart rate or individual beats' EKG complexes, among others.

The patient index can be a value derived directly from the signal relating to the first cardiac activity or the signal relating to the first body movement. For example, one or more heart rate values can be derived from a cardiac activity signal over one or more periods of time. For example, as described in U.S. patent application Ser. No. 12/770,562, filed Apr. 29, 2010, a foreground heart rate over a relatively short time period (e.g., 5-30 sec) and a background heart rate over a longer time period (e.g., 30-600 sec) can both be derived from a cardiac activity signal. For another example, an accelerometer or inclinometer mounted on a patient's body can give information about the patient's (and/or parts of his body) movements and body position, such as are described in more detail in U.S. patent application Ser. No. 12/896,525, filed Oct. 1, 2010.

The patient index can also be a determination of an epileptic event. For example, the cardiac activity and/or body movement can be analyzed to determine an occurrence of an epileptic event, a non-occurrence of an epileptic event, or a probable occurrence of an epileptic event.

In one embodiment, triggering the test(s) can be based on at least one of a patient's cardiac activity and the patient's body movement upon a finding that the cardiac activity and/or body movement are indicative of a possible epileptic event. For example, if the cardiac activity and/or body movement clearly indicate an epileptic event with high confidence, triggering the test(s) need not be performed; but if the cardiac activity and/or body movement are outside their interictal reference value ranges but have values that give only low confidence of an epileptic event, triggering can be performed to provide additional information about the patient's condition to indicate whether he or she is suffering an epileptic event or not.

For another example, the patient's cardiac activity at a first time may indicate an epileptic event, and the patient's body movement at a second time and in a particular region of the body may indicate an epileptic event, but if the two times differ, or the body movement is in a different region of the body, or changes in their characteristics (e.g., rate, morphology, pattern, etc.) are discordant with declaring the epileptic event, consideration of cardiac activity and body movement may lead to low confidence of an indication of an epileptic event, and in response thereto, triggering of additional test(s) and/or consideration of additional body signals may be desirable. In other words, there may be a low absolute value of correlation (e.g., a correlation between about −0.4 and 0.4) between the patient's cardiac activity and the patient's body movement that would prevent highly confident determination of an epileptic event. The triggered test(s) may provide enough additional information to make a highly confident determination of an epileptic event (or the non-occurrence of an epileptic event).

Generally, two parameters can be considered highly correlated if the coefficient of correlation is greater than about 0.7, and lowly correlated if the coefficient of correlation is less than about 0.4. Two parameters can be considered highly anticorrelated if the coefficient of correlation is less than about −0.7, and lowly anticorrelated if the coefficient of correlation is greater than about −0.4. One example of parameters/situations that can be considered to be anticorrelated includes an appearance of tachycardia with a disappearance of body movement. Other examples that can be considered to be anticorrelated are a strong body movement with either a substantially unchanged heart rate or a decreased heart rate. The example with the substantially unchanged heart rate can be considered a low anticorrelation, and the example with the decreased heart rate can be considered a high anticorrelation.

Another pair of examples to consider are the correlations between body movement and first derivative of heart rate in an epileptic event vs. in exercise. Generally, the first derivative of heart rate is greater in an epileptic event than in exercise, i.e., body movement and the first derivative of heart rate can be considered more highly correlated in epileptic events than in exercise.

The presence of either high or low correlation or anticorrelations may be used in this invention to determine the occurrence of an epileptic event and trigger an action(s) or to determine that an epileptic event is not occurring or did not occur. The first and second cardiac activity may be the same (in other words, triggering can be of a second iteration of a test that reported the first cardiac activity as a result of a first iteration, giving a more current value of the cardiac activity), or they may be different. In one embodiment, the first cardiac activity is heart rate or heart rate variability, and the second cardiac activity is heart beat morphology.

Similarly, the first and second body movement may be the same, or they may be different.

A "test" is used herein to refer to any assay of the patient's cardiac activity, body movement, responsiveness, awareness, or a spectral analysis thereof. The product of a test can be considered a signal, and a signal can be considered as resulting from a test. A test of the second cardiac activity may use substantially the same data source, data processing, and/or related techniques as are used in receiving the signal relating to the first cardiac activity. In another embodiment, the techniques may differ. For example, the first cardiac activity can be heart beat morphology determined by electrocardiography (EKG), and the second cardiac activity can be heart beat morphology determined by phonocardiography (PKG).

Similarly, a test of the second body movement may, but need not, use substantially the same data source, data processing, and/or related techniques as are used in receiving the signal relating to the first body movement.

The concept of first and second cardiac activity or first and second body movement is also applicable to responsiveness and awareness. For example responsiveness activity may be a reflex movement such as withdrawal from a source of painful stimuli and a second responsiveness activity may be a complex movement such as that required to draw a triangle. Different tests of varying levels of complexity may be administered to test responsiveness as defined in this invention.

The particular triggered test(s) may be selected based at least in part on the first cardiac activity, the first body movement, or both.

In one embodiment, determining is based on at least one of a finding the patient's awareness differs from a reference responsiveness level, a finding the patient's awareness differs from a reference awareness level, a finding the patient's second cardiac activity includes a characteristic suggestive of an epileptic event, a finding the spectral analysis of the patient's second cardiac activity includes a characteristic suggestive of an epileptic event, and a finding the spectral analysis of the patient's second body movement includes a characteristic suggestive of an epileptic event.

Figure 10:
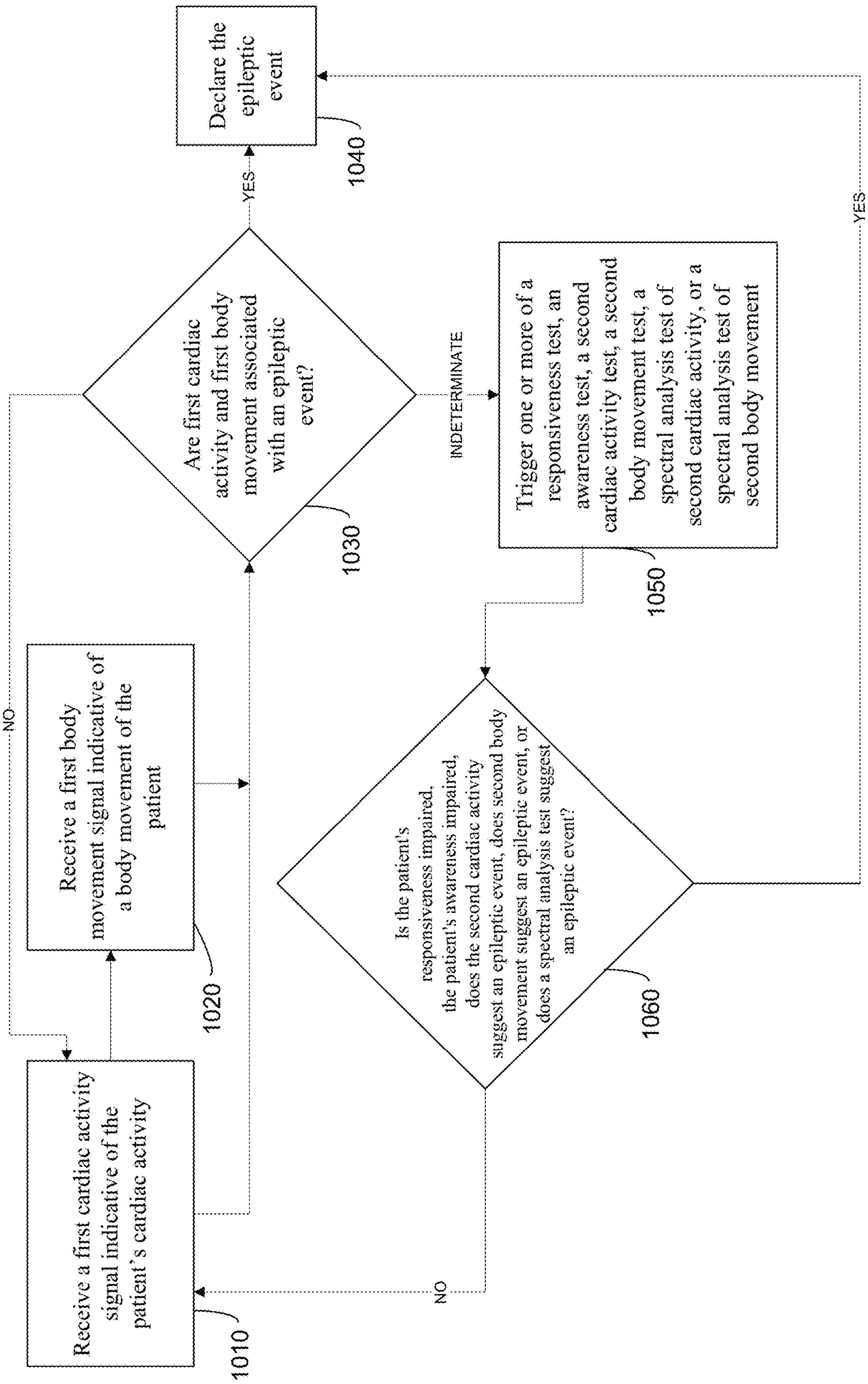
FIG. 10 shows a flowchart of an implementation of a method according to one embodiment of the present invention.

FIG. 10 shows a flowchart depicting one embodiment of a method according to the present invention. A cardiac activity signal indicative of the patient's cardiac activity is received at block 1010 and/or a body movement signal indicative of a body movement of the patient is received at block 1020.

Thereafter, a determination is made in block 1030 whether cardiac activity and body movement are associated with an epileptic event. If no, flow returns to the receiving blocks 1010-1020. If yes, an epileptic event is declared at block 1040. However, if no determination can be made, flow moves to block 1050, where one or more of a responsiveness test, an awareness test, a second cardiac activity test, a second body movement test, a spectral analysis test of the second cardiac activity, or a spectral analysis test of the second body movement, are triggered.

Thereafter, a determination is made in block 1060 whether the patient's responsiveness, awareness, second cardiac activity, second body movement, and/or spectral analysis of second cardiac activity or second body movement are indicative of an epileptic event. If no, flow returns to the receiving blocks 1010-1020. If yes, an epileptic event is declared at block 1040.

Alternatively or in addition to declaring an epileptic event, further actions can be performed. In one embodiment, the method further comprises classifying the epileptic event based upon at least one of the first cardiac activity, the first body movement, the responsiveness, the awareness, the second cardiac activity, the second body movement, the spectral properties of the second cardiac activity, the spectral properties of the second body movement, and two or more thereof.

Classifications of epileptic events can be generally based on the information shown in FIGS. 4-7 and the discussion herein and in U.S. patent application Ser. No. 12/896,525, filed Oct. 1, 2010. Classifications can also be based in part on observations of stereotypical seizures of a particular patient. Not all seizures that a clinician would recognize as being of a particular type may exhibit all the properties discussed herein, and thus, not all may be amenable to classification by the methods described herein, but a substantial majority are expected to be amenable to classification by the methods described herein.

In one embodiment, the epileptic event is classified as a generalized tonic-clonic seizure when the following occur in a patient in a first, non-recumbent position: the first body movement comprises a fall from the first, non-recumbent position, wherein (i) the fall is associated with a loss of responsiveness, a loss of awareness, or both; and (ii) the fall is followed by generalized body movements.

Falls to the ground associated with a primarily or secondarily generalized tonic-clonic, generalized tonic, generalized clonic-tonic-clonic seizure or generalized atonic seizure are distinguishable from those caused by tripping or slipping by the absence of protective/defensive actions (e.g., breaking the fall with the arms) and other features such which body part(s) is(are) first on contact with the ground.

Primarily generalized seizures usually result in synchronous bilateral movements of equal amplitude, with maintenance of head and eyes on the midline. Secondarily generalized seizures usually manifest at onset with unilateral movements of limbs, head, eyes, or trunk.

In one embodiment, the generalized body movement comprises a rhythmic body movement. Alternatively or additionally, the generalized body movements can comprise flexion and extension of joints and/or can have a frequency of about 3 Hz at some time during the epileptic event. In another embodiment, the rhythmic movement is temporally associated with an epileptiform discharge.

Body movement can allow classification of an epileptic event as to primarily generalized or secondarily generalized. Specifically, the epileptic event can be classified as primarily generalized if body movements are synchronous and of equal amplitude on both sides of the body, and as secondarily generalized if not.

In a further embodiment, the epileptic event is classified as a generalized tonic-clonic seizure when recovery of awareness follows recovery of responsiveness, provided at least one of the key identifiers (e.g., loss of postural tone or diffuse increase in muscle tone or rhythmical body movements) have occurred.

In one embodiment, the epileptic event is classified as an atonic seizure when the following occur in a patient in a first, non-recumbent position:

i) a body movement comprises a fall from the first, non-recumbent position, wherein the fall is associated with a loss of responsiveness, a loss of awareness, or both; and (ii) the patient shows a significant reduction in body movements below a reference value after the fall, a significant reduction in muscle tone below a reference value after the fall, or both.

Typically, the significant reductions in body movements and/or muscle tone commonly seen in atonic seizures are not caused by changes in heart or respiratory activity.

In one embodiment, the epileptic event is classified as tonic when the following occur to a patient in a first, non-recumbent position: an increase in muscle tone above a reference value, a loss of responsiveness, and an absence of generalized movements.

In a further embodiment, the epileptic event is classified as tonic when recovery of awareness follows recovery of responsiveness, provided it has been associated with loss of responsiveness or awareness.

In one embodiment, the epileptic event is classified as a complex partial seizure based upon a finding the patient's cardiac activity is associated with impaired awareness and is not associated with a fall or at some point in time with generalized rhythmical body movements; and the epileptic event is classified as a simple partial seizure based upon a finding the patient's cardiac activity is not associated with impaired awareness and is not associated with generalized rhythmical body movements.

In one embodiment, the event is classified as syncope, when at least one of the following occur: the body movement comprises a fall from a non-recumbent position and the fall is associated with a loss of responsiveness or a loss of awareness, and recovery of responsiveness or recovery of awareness occurs immediately after the fall, or when the body movement comprises a fall from a recumbent position, there is marked decrease in heart rate or a brief transient cessation of heart beats (asystole).

Epileptic events can be determined or classified in view of the patient's body position. For example, an epileptic event when the patient is in a decubitus position (lying down) may be determined from an observation of transient loss of muscle tone in antigravitatory muscles (e.g., paraspinal; quadriceps), followed by transient increase in muscle tone in agonist and antagonist muscle groups (e.g., paraspinal and abdominal recti; quadriceps and hamstrings), which in turn is followed by generalized rhythmical muscle contractions (typically with a frequency of 3 Hz and/or 10-12 Hz at some time during the event).

For another example, an epileptic event when the patient is in a seated position may be determined using both electromyography (EMG) signals and accelerometer signals.

The one or more of the first cardiac activity, the second cardiac activity, the first body movement, the second body movement, the responsiveness, and the awareness can be provided by any known technique. In one embodiment, at least one of the first cardiac activity and the second cardiac activity is sensed by at least one of an electrocardiogram (EKG), phonocardiogram (PKG), apexcardiography, blood pressure monitor, and echocardiography. The body movement can be sensed by any known technique. In one embodiment, at least one of the first body movement and the second body movement is sensed by an accelerometer, an inclinometer, an actigraph, an imaging system, a dynamometer, a gyroscope, electromyography (EMG), or two or more thereof.

In certain circumstances, the method can make a false positive determination of an epileptic event, i.e., determine an epileptic event based on the signals and tests described above when no epileptic event (as may be determined using direct/invasive recording of electrical activity at/near the epileptogenic zone, observation by a skilled practitioner, or other techniques known to the person of ordinary skill in the art) occurred. In one embodiment, the method further comprises receiving an indication that the determined epileptic event was not an actual epileptic event. Such indications may include, but are not limited to, the first body movement is a fall but the fall is not characteristic of an epileptic fall; the generalized body movements are not rhythmical and bilaterally synchronous; the generalized body movement have a frequency substantially different from 3 Hz or a variable frequency; the generalized body movements change direction, pairs of agonist-antagonist muscles, and/or movements in different directions occur simultaneously in two or more joints; the change in cardiac activity, cardiac activity morphology, cardiac spectral analysis, apexcardiography, or echocardiography is not characteristic of epileptic seizures.

Similarly, in one embodiment, the method further comprises receiving an indication of a false negative, i.e., an indication an epileptic event occurred but no determination thereof was made.

The indication may be based at least in part on input from the patient, a caregiver, or a medical professional, and/or on quantification or characterization of one or more body signals. The indication may be provided at the time of the false determination or later.

A false determination (whether positive or negative) may render it appropriate to modify the body signals or analyses used in making future determinations. In one embodiment, the method further comprises reducing a likelihood of a future determination of a false positive epileptic event based at least in part on one or more of the first cardiac activity, the first body movement, the responsiveness, the awareness, the second cardiac activity, the second body movement, the spectral analysis of the second cardiac activity, or the spectral analysis of the second body movement, in response to the indication. In another embodiment, the method further comprises reducing a likelihood of a future determination of a false negative epileptic event based at least in part on one or more of the first cardiac activity, the first body movement, the responsiveness, the awareness, the second cardiac activity, the second body movement, the spectral analysis of the second cardiac activity, or the spectral analysis of the second body movement, in response to the indication.

When an epileptic event is determined, the method can further comprise one or more of logging the occurrence and/or time of occurrence of the seizure; providing a warning, alarm or alert to the patient, a caregiver or a health care provider; providing a therapy to prevent, abort, and/or reduce the severity of the seizure; assessing one or more patient parameters such as awareness or responsiveness during the seizure; assessing the severity of the seizure; identifying the end of the seizure; and assessing the patient's post-ictal impairment or recovery from the seizure. "Recovery" is used herein to encompass a time after seizure onset and/or seizure end when the patient's parameters are returning to baseline. Other examples include, but are not limited to, logging one or more of a time of onset of the epileptic event, a time of termination of the epileptic event, a severity of the epileptic event, an impact of the epileptic event, an interval between the epileptic event and the most recent preceding epileptic event, an epileptic event frequency over a time window, an epileptic event burden over a time window, time spent in epileptic events over a time window, or a type of epileptic event.

To reduce the rate of false positive detections or for other reasons, in one embodiment, the method further comprises recording one or more of the patient's reference body movement or movements, reference cardiac activity, reference responsiveness level, reference awareness level, reference cardiac activity, reference spectral analysis of the cardiac activity, or reference spectral analysis of the body movement during one or more interictal activities at one or more times when the patient is not suffering an epileptic event, to yield recorded data not associated with an epileptic event; defining one or more interictal activity reference characteristics from the recorded data; and overruling the determination of the epileptic event based at least in part on finding the patient's first body movement, first cardiac activity, responsiveness level, awareness level, second cardiac activity, second body movement, spectral analysis of the second cardiac activity, and spectral analysis of the second body movement matches the one or more interictal event reference characteristics.

The interictal activities at one or more times when the patient is not suffering an epileptic event can include different activities (e.g., walking vs. running vs. swimming, etc.), and can alternatively or in addition include the same activity at different times of day, week, month, or year, or under different external circumstances (e.g., walking at sea level vs. walking at higher altitude, etc.).

The overruling of a determination of an epileptic event may be made with some probability between zero and one. The overruling may be made according to a permanent or semipermanent rule or on a case-by-case basis. The references may be stored in a library on a per-patient, per-seizure type, or per-population basis.

In one embodiment, the overruling may involve the triggering of one or more additional test(s). Such further triggering may allow more accurate determination of epileptic events.

Recording one or more of the patient's reference body movement or movements, reference cardiac activity, reference responsiveness level, reference awareness level, reference cardiac activity, reference spectral analysis of the cardiac activity, or reference spectral analysis of the body movement during epileptic event may allow overruling of false negative or false positive determinations.

The body movement during one or more interictal activities can include at least one of a movement of a part of the body (e.g., the eyes or eyelids), a movement of a limb (e.g., an arm), a movement of a part of a limb (e.g., a wrist), a direction of a movement, a velocity of a movement, a force of a movement, an acceleration of a movement, a quality of a movement, an aiming precision of a movement, or a purpose or lack thereof of a movement.

The likelihood of a patient suffering an epileptic event may change at different times and/or under different conditions. In one embodiment, a plurality of interictal event reference characteristics are defined which differ from one another based on one or more of the time of day of the recording, the time of week of the recording, the time of month of the recording, the time of year of the recording, the type of activity, changes in the patient's body weight or body mass index, changes in the patient's medication, changes in the patient's physical fitness or body integrity, state of physical or mental health, mood level or changes in the patient's mobility. Alternatively or in addition, a plurality of interictal event reference characteristics in a female patient can be defined in reference to the menstrual cycle and/or to pregnancy. Alternatively or in addition, changes in the patient's environment may change the likelihood of the patient suffering an epileptic event.

In a further embodiment, the overruling is based at least in part on one or more of the plurality of interictal event reference characteristics.

Any characteristic of the one or more interictal events may be considered. In one embodiment, the one or more characteristics are patterns or templates.

It may be desirable in certain embodiments to adapt at least one of a reference value on one or more of the body movement, the cardiac activity, the responsiveness level, the awareness level, the second cardiac activity, the second body movement, and the spectral analysis of cardiac activity or body movement, based upon one or more determinations that the specificity of past detections was above or below a specificity measure, the sensitivity of past detections was above or below a sensitivity measure, the speed of detection defined as the time elapsed between the occurrence of the first body signal change indicative of the onset of the seizure and the issuance of the detection, the cost of the therapy was below or above a cost measure, the patient's tolerance of the therapy was below an acceptable tolerance, the adverse effects were above an acceptable level, or the patient's disease state was below or above a first disease state threshold. Positive predictive value or negative predictive value may be used in addition to or instead of specificity or sensitivity.

As should be apparent, a single "threshold" can be mathematically defined in a number of ways that may be above or below a particular value of a particular parameter. For example, an elevated heart rate can be defined, with equal validity, as a heart rate above a threshold in units of beats/unit time or an interbeat interval below a threshold in units of time. More than one "threshold" may be used to optimize specificity, sensitivity or speed of detection.

For example, the method can further comprise determining one or more of a specificity of past detections, a sensitivity of past detections, a speed of past detections, a cost of a therapy for epileptic events, a patient's tolerance of a therapy for epileptic events, and a disease state of the patient; and loosening at least one constraint on one or more of the body movement, the cardiac activity, the responsiveness test, the awareness test, the second cardiac activity test, the second body movement test, and the spectral analysis of second cardiac activity or second body movement based upon one or more determinations that the specificity of past detections was above a first specificity threshold, the sensitivity of past detections was below a first sensitivity threshold, the speed of detection was below a first speed of detection threshold, the cost of the therapy was below a first cost threshold, the patient's tolerance of the therapy was below a first tolerance threshold (i.e., the patient can tolerate more detections or actions performed in response to detections), and the patient's disease state was below a first disease state threshold; or tightening the at least one constraint based upon one or more determinations that the specificity of past detections was below a second specificity threshold, the sensitivity of past detections was above a second sensitivity threshold, the speed of detection was above an acceptable threshold for efficacy of therapy and safety of the patient, the cost of the therapy was above a second cost threshold, the patient's tolerance of the therapy was above a second tolerance threshold (i.e., the patient cannot tolerate more detections or actions performed in response to detections), and the patient's disease state was above a second disease state threshold.

In another embodiment, the invention can be used for the detection of generalized tonic-clonic seizures. A "generalized tonic-clonic seizure" is used herein to refer to a primarily or secondarily generalized seizure that features at least one tonic, clonic, or both tonic and clonic phase. Myoclonic seizures are included in this definition. At onset or at some point during the generalized tonic-clonic seizure, at least a majority of the body muscles or joints are involved. "Body muscle" is used herein to refer to those capable of moving joints, as well as muscles of the eyes, face, oropharyngeal, pharyngeal, abdominal, and respiratory systems.

In one embodiment, the present invention relates to a method, comprising:

- receiving at least two body signals selected from the group consisting of a signal relating to a first body movement, a signal relating to a first cardiac activity, a responsiveness signal, an awareness signal, a signal relating to a second cardiac activity, a signal relating to a second body movement, a spectral analysis signal relating to the second cardiac activity, and a spectral analysis signal relating to the second body movement;
- determining an occurrence of a generalized tonic-clonic epileptic seizure, the determination being based upon the correlation of at least two features, at least one feature being of each of the at least two body signals, wherein:
  - the feature of the first cardiac activity signal is an increase in the patient's heart rate above an interictal reference value;
  - the feature of the first body movement signal is at least one of (i) an increase in axial or limb muscle tone substantially above an interictal or exercise value for the patient, (ii) a decrease in axial muscle tone in a non-recumbent patient, below the value associated with a first, non-recumbent position, (iii) fall followed by an increase in body muscle tone, or (iv) a fall followed by generalized body movements;
  - the feature of the responsiveness signal is a decrease in the patient's responsiveness below an interictal reference value;
  - the feature of the awareness signal is a decrease in the patient's awareness below an interictal reference value;
  - the feature of the second cardiac activity signal is a correlation with an ictal cardiac activity reference signal;
  - the feature of the second body movement signal is a correlation with an ictal body movement reference signal;
  - the feature of the spectral analysis signal of the second cardiac activity is a correlation with an ictal cardiac activity spectral analysis reference signal; or
  - the feature of the spectral analysis signal of the second body movement is a correlation with an ictal body movement spectral analysis reference signal;

and
- performing a further action in response to the determination of the occurrence of the epileptic event.

Figure 11:
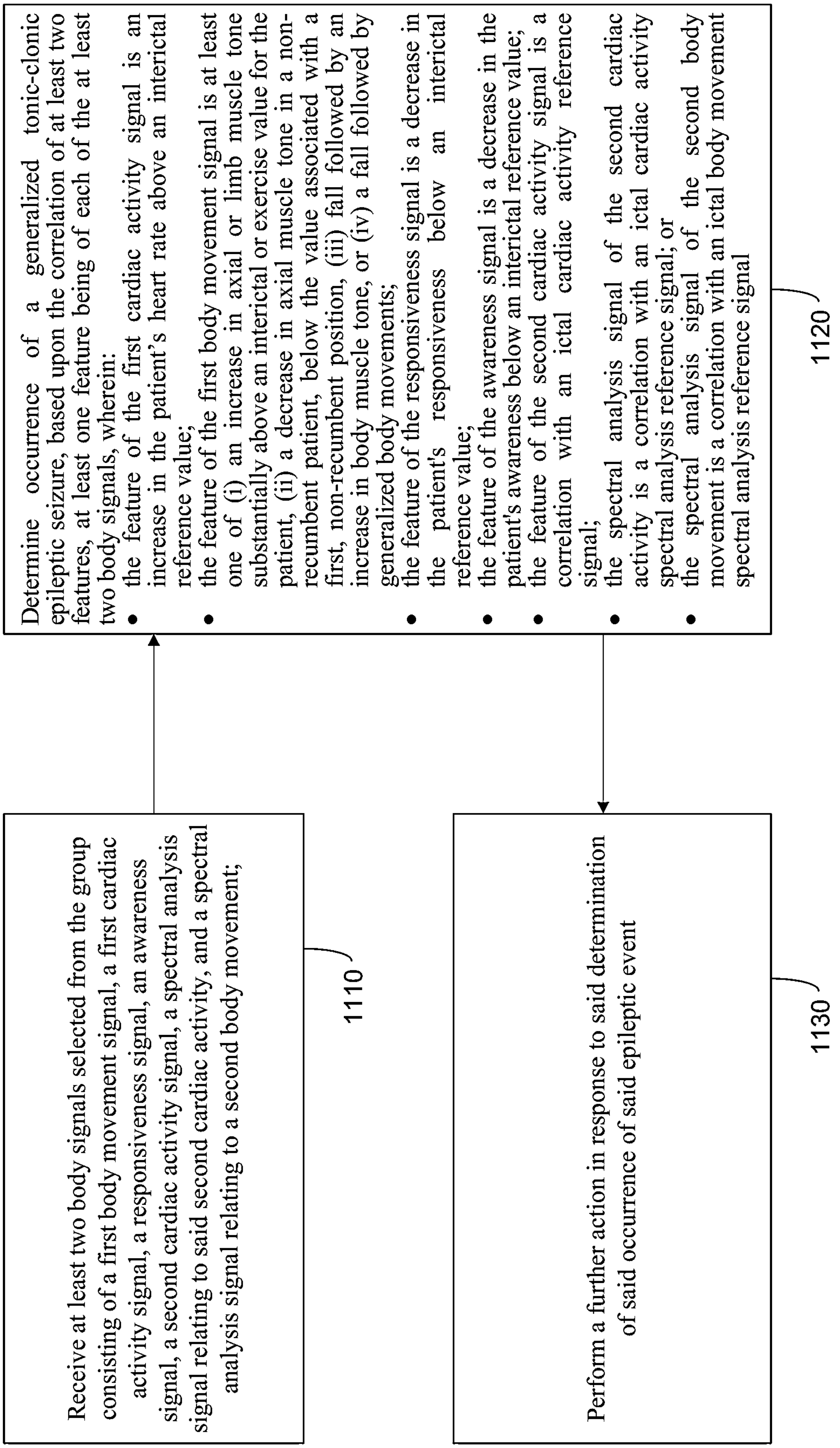
FIG. 11 shows a flowchart of an implementation of a method according to one embodiment of the present invention.

FIG. 11 depicts one embodiment of this method. FIG. 11 depicts a receiving step 1110, a determining step 1120, and a performing step 1130.

In one embodiment, the correlation has a high absolute value and is either positive or negative. E.g. the correlation may be positive, such as with a value greater than 0.7, 0.75, 0.8, 0.85, 0.9, or 0.95, or negative, such as with a value less than −0.7, −0.75, −0.8, −0.85, −0.9, or −0.95.

The further action may comprise one or more of logging the occurrence and/or time of occurrence of the seizure; providing a warning, alarm or alert to the patient, a caregiver or a health care provider; providing a therapy to prevent, abort, and/or reduce the severity of the seizure; assessing one or more patient parameters such as awareness or responsiveness during the seizure; assessing the severity of the seizure, identifying the end of the seizure; and assessing the patient's post-ictal impairment or recovery from the seizure.

The various signals can be provided by any appropriate technique and their features referred to above can likewise be measured as a routine matter for the person of ordinary skill in the art having the benefit of the present disclosure. For example, in one embodiment, the correlation of the second cardiac activity signal with the ictal cardiac activity reference signal comprises a match to an ictal cardiac activity template;

- the correlation of the second body movement signal with the ictal body movement reference signal comprises a match to an ictal body movement template;
- the correlation of the spectral analysis signal of the second cardiac activity with the ictal cardiac activity spectral analysis reference signal comprises a match to an ictal cardiac activity spectral analysis pattern or template; or
- the correlation of the spectral analysis signal of the second body movement with the ictal body movement spectral analysis reference signal comprises a match to an ictal body movement spectral analysis pattern or template.

Aspects of the signals and their features may include, among others, a body movement signal further comprising an indication of a fall prior to the indication of the tonic or clonic activity.

In one embodiment, a tonic-clonic seizure can be further characterized as secondarily generalized if the first body movement signal does not comprise synchronous movement of all body muscles with equal amplitude or velocity prior to an indication of tonic or clonic activity.

In one embodiment, the end of the generalized tonic-clonic epileptic seizure can be indicated when at least one of the body signals trends toward an interictal reference value, range, or pattern of the body signal.

In one embodiment, the method further comprises indicating the beginning of a post-ictal period based upon the appearance of at least one post-ictal feature of at least one the body signal, wherein:

the post-ictal feature of the first cardiac signal or the second cardiac signal is a decrease in the patient's heart rate below an ictal reference value;

the post-ictal feature of the first body movement signal or the second body movement signal is a decrease in the patient's muscle tone or movement below an ictal reference value;

the post-ictal feature of the responsiveness signal is an increase in the patient's responsiveness above an ictal value and below an inter-ictal reference value; or the post-ictal feature of the awareness signal is an increase in the patient's awareness above an ictal value and below an inter-ictal reference value.

The term "post-ictal," is not necessarily limited to the period of time immediately after the end of the primarily or secondarily generalized tonic-clonic epileptic seizure and is not limited to this type of seizure but also encompasses partial seizures (e.g., all complex and certain simple partial and absence seizures). Rather, it refers to the period of time during which at least one signal has one or more features that differs from the ictal and inter-ictal reference values that indicates one or more of the patient's body systems are not functioning normally (e.g., as a result of the seizure or of an injury suffered during the seizure) but are not exhibiting features indicative of a seizure.

In one embodiment, the end of the post-ictal period can be indicated when each of the post-ictal features is outside the range of values associated with the ictal and post-ictal states. In another embodiment, the end of the post-ictal period can be indicated when at least one of the post-ictal features is outside the range of values associated with the ictal and post-ictal states. In this embodiment, the onset and termination of the post-ictal period may be partial when all features have not returned to interictal reference values or complete when all features have. This distinction (partial vs. complete) has important therapeutic (the patient may require treatment until all body signals have fully recovered to inter-ictal values), safety (the patient's mortality and morbidity risks may remain increased until all body signal have fully recovered to inter-ictal values) and predictive implications (the probability of occurrence of the next seizure and time to it (inter-seizure interval) may depend on recovery of one more body signals to their interictal value.

It should also be borne in mind that different features are expected to return to their interictal reference values at different times. For example, from kinetic and brain electrical perspectives, a seizure can be defined as having ended when abnormal movements and abnormal EEG cease. These events typically take place before the patient's heart rate returns to baseline. Further, it may take a few minutes after abnormal movements and abnormal EEG end for cognition and responsiveness to return to baseline; up to about 30 min for awareness to return to baseline; and about 30-45 min for blood lactic acid concentration to return to baseline. Temporal relationships between changes in signal features, and transitions from one state to another, are generally described in U.S. patent application Ser. No. 12/896,525, filed Oct. 1, 2010. Transitions may have quantifiable differences in location as well, e.g., the number of either brain sites or body organs in which the transition has taken place may vary over time (e.g., an ictal change first occurring on the right mesiotemporal lobe, or a change in heart activity at or near seizure onset followed by changes in metabolic indices.

In another embodiment, the present invention relates to the detection of partial seizures. In one embodiment, the present invention relates to a method, comprising:

receiving at least two body signals selected from the group consisting of a signal relating to a first body movement, a signal relating to a first cardiac activity, a responsiveness signal, an awareness signal, a signal relating to a second cardiac activity, a signal relating to a second body movement, a spectral analysis signal relating to the second cardiac activity, and spectral analysis signal relating to the second body movement; and determining an occurrence of a partial epileptic seizure based upon a correlation of two features, at least one feature being of each of the at least two body signals, wherein:

the feature of the first cardiac signal is a value outside an interictal reference value range;

the feature of the first body movement signal is a body movement associated with a partial seizure;

the feature of the second cardiac activity signal is a correlation with an ictal cardiac activity reference signal;

the feature of the second body movement signal is a correlation with an ictal body movement reference signal;

the feature of the spectral analysis signal of the second cardiac activity is a correlation with an ictal cardiac activity spectral analysis reference signal; or the feature of the spectral analysis signal of the second body movement is a correlation with an ictal body movement spectral analysis reference signal; and performing a further action in response to the determination of the occurrence of the epileptic event.

Figure 12:
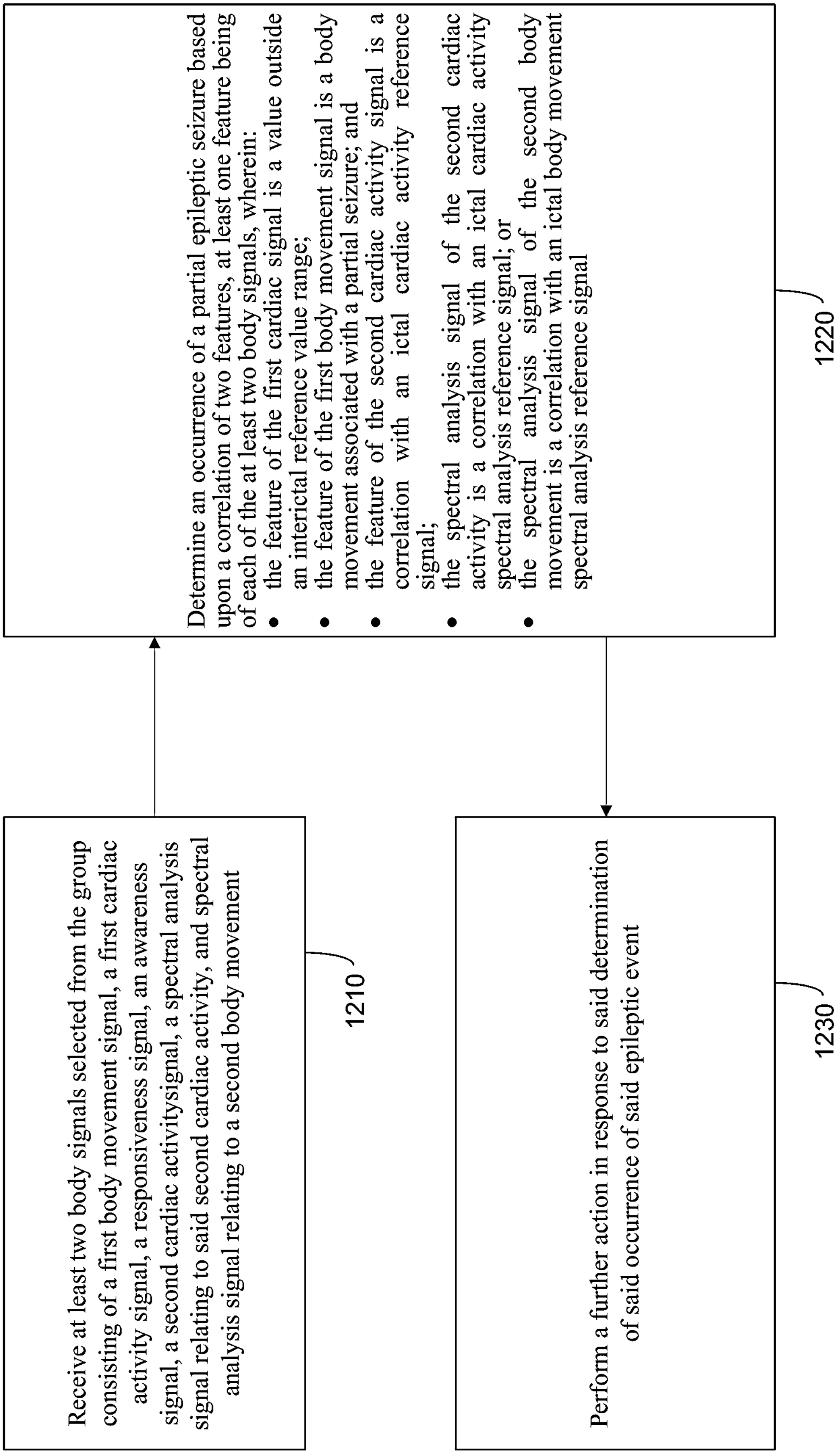
FIG. 12 shows a flowchart of an implementation of a method according to one embodiment of the present invention.

FIG. 12 depicts one embodiment of this method. FIG. 12 depicts a receiving step 1210, a determining step 1220, and a performing step 1230.

The various signals can be provided by any appropriate technique and their features referred to above can likewise be measured as a routine matter for the person of ordinary skill in the art having the benefit of the present disclosure. For example, in one embodiment, the correlation of the second cardiac activity signal with the ictal cardiac activity reference signal comprises a match to an ictal cardiac activity template;

the correlation of the second body movement signal with the ictal body movement reference signal comprises a match to an ictal body movement template;

the correlation of the spectral analysis signal of the second cardiac activity with the ictal cardiac activity spectral analysis reference signal comprises a match to an ictal cardiac activity spectral analysis pattern or template; or the correlation of the spectral analysis signal of the second body movement with the ictal body movement spectral analysis reference signal comprises a match to an ictal body movement spectral analysis pattern or template.

Matches to patterns and templates are described in U.S. patent application Ser. No. 12/884,051, filed Sep. 16, 2010. A "match" should not be construed as requiring a complete or perfect fit to a pattern or template.

In one embodiment, the further action comprises one or more of logging the occurrence and/or time of occurrence of the seizure; providing a warning, alarm or alert to the patient, a caregiver or a health care provider; providing a therapy to prevent, abort, and/or reduce the severity of the seizure; assessing one or more patient parameters such as awareness or responsiveness during the seizure; assessing the severity of the seizure, identifying the end of the seizure; and assessing the patient's post-ictal impairment or recovery from the seizure.

Partial seizures generally result in body movements that do not include falls.

The partial seizure can be classified as (i) complex if at least one of the features of the awareness signal is a decrease in the patient's awareness below its reference value, or as (ii) simple if there is no decrease in the patient's awareness below its reference value, or if there is a decrease in the patient's responsiveness but awareness remains at an interictal value.

In one embodiment, the end of the partial epileptic seizure can be indicated when at least one of the features of the respective body signals is outside the range of values associated with the ictal state for that body signal. In another embodiment, the end of the partial epileptic seizure can be indicated when each of the features of the respective body signals trends toward an interictal reference value, range, or pattern of the body signal.

In one embodiment, the method further comprises indicating the beginning of a post-ictal period when at least one of the body signals is outside the range of values associated with the ictal and inter-ictal states for that body signal, wherein:

the post-ictal feature of the cardiac signal is a heart rate outside the range of values associated with the ictal state;

the post-ictal feature of the body movement signal is a change in the patient's movement outside the ictal range of values;

the post-ictal feature of the responsiveness signal is an increase in the patient's responsiveness above an ictal reference value but remaining below an inter-ictal reference value; and the post-ictal feature of the awareness signal is an increase in the patient's awareness above an ictal reference value but remaining below an inter-ictal reference value.

In one embodiment, the end of the post-ictal period can be indicated when at least one of the post-ictal features is absent from its respective body signal.

In one embodiment, such responsive action(s) may be taken if the ictal or postictal state's severity exceeds a threshold, e.g., the $90^{th}$ percentile values for a patient.

Various responsive actions, such as warning, logging, and treating, among others, are generally described in U.S. patent application Ser. No. 12/896,525, filed Oct. 1, 2010. A warning may be graded, e.g., a yellow light for a mild seizure, a red light for a severe one. Treating can comprise providing supporting treatment (e.g., fluids, oxygen).

Seizure severity indices may be calculated and stored by appropriate techniques and apparatus. More information on seizure severity indices is available in U.S. patent application Ser. No. 13/040,996, filed Mar. 4, 2011.

In one embodiment, the present invention relates to a system, comprising:

at least one sensor configured to receive at least one of a signal relating to a first cardiac activity from a patient, a signal relating to a first body movement from the patient, a responsiveness signal from the patient, an awareness signal from the patient, a signal relating to a second cardiac activity of the patient, and a signal relating to a second body movement of the patient;

a detection unit configured to receive the at least one signal from the at least one sensor and determine an occurrence of an epileptic event; and an action unit configured to receive an indication of the occurrence of the epileptic event from the detection unit and perform at least one of logging the occurrence and/or time of occurrence of the epileptic event; providing a warning, alarm or alert to the patient, a caregiver or a health care provider; providing a therapy to prevent, abort, and/or reduce the severity of the epileptic event; assessing one or more patient parameters such as awareness or responsiveness during the epileptic event; assessing the severity of the epileptic event, identifying the end of the epileptic event; and assessing the patient's post-ictal impairment or recovery from the epileptic event.

The system can further comprise other units. For example, the system can comprise a spectral analysis unit configured to generate at least one spectral analysis signal from the signal relating to the second cardiac activity and/or the signal relating to the second body movement. In this embodiment, it may be desirable for the detection unit to be further configured to receive the at least one spectral analysis signal from the spectral analysis unit.

Although not limited to the following, exemplary systems capable of implementing embodiments of the present invention are generally discussed below and in U.S. patent application Ser. No. 12/896,525, filed Oct. 1, 2010.

FIG. 1A depicts a stylized system comprising an external unit 145*a* capable of receiving, storing, communicating, and/or calculating information relating a patient's epileptic events. The system shown in FIG. 1A also includes at least one sensor 212. The sensor 212 may be configured to receive cardiac activity data, body movement data, responsiveness data, awareness data, or other data from the patient's body. A lead 211 is shown allowing communication between the sensor 212 and the external unit 145*a*.

Figure 1B:
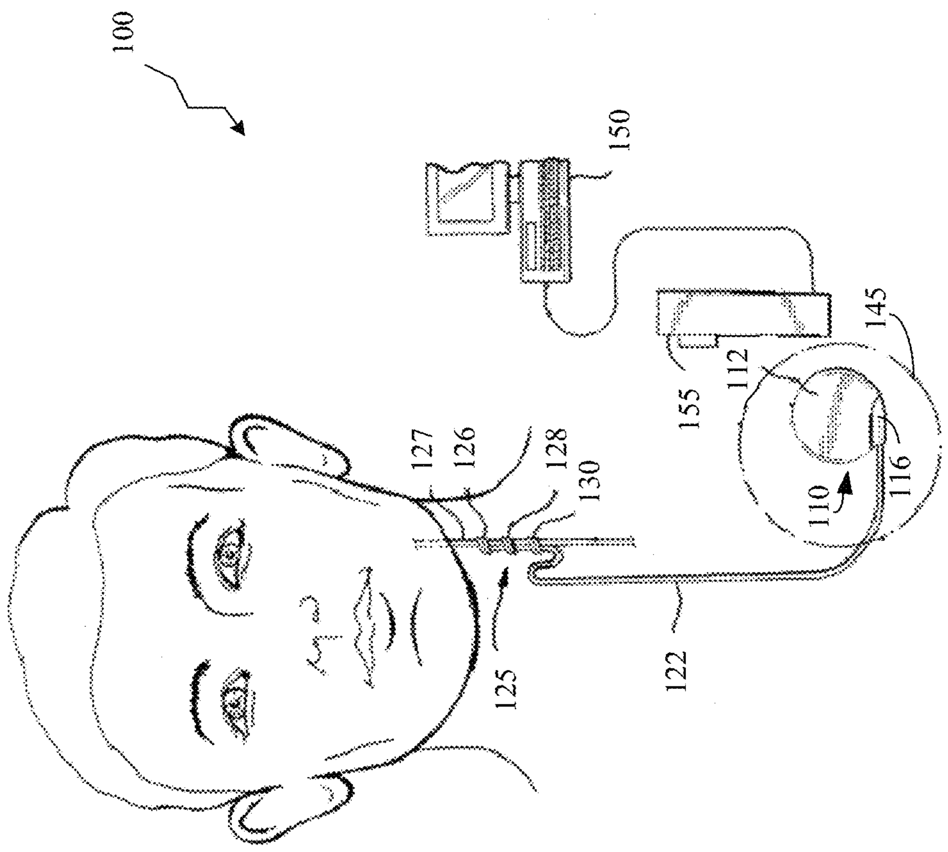

FIG. 1B depicts a stylized implantable medical system (IMD) 100, similar to that shown in FIG. 1 of U.S. patent application Ser. No. 12/896,525, filed Oct. 1, 2010, and discussed therein.

Figure 2:
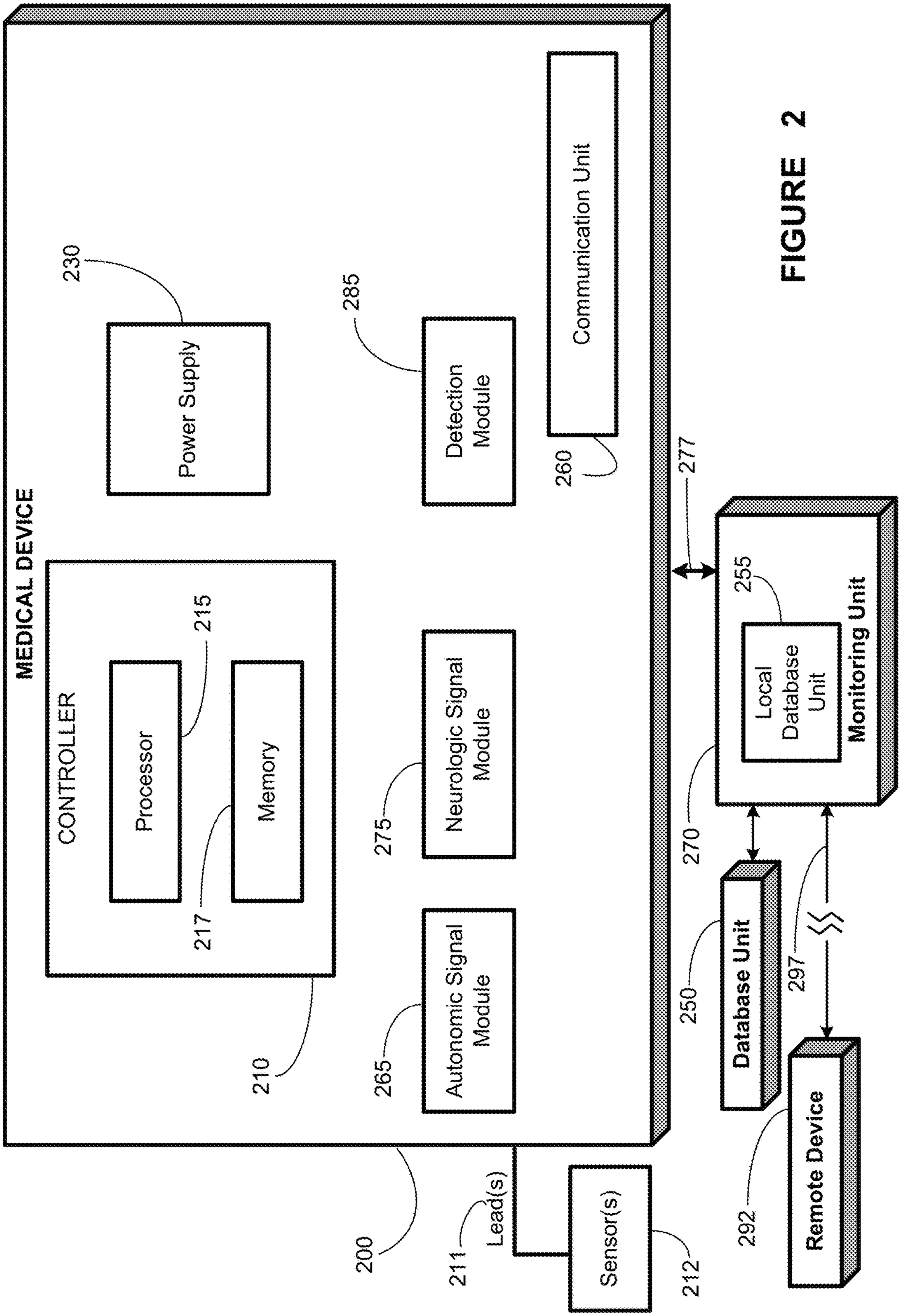
FIG. 2 provides a block diagram of a medical device system that includes a medical device and an external unit, in accordance with one illustrative embodiment of the present invention.

FIG. 2 is shown and generally described in U.S. patent application Ser. No. 12/896,525, filed Oct. 1, 2010. As is apparent to the person of ordinary skill in the art, the neurological signal module 275 is capable of collecting neurological data and providing the collected neurological data to a detection module 285.

In other embodiments (not shown), other types of signals may be collected and provided to the detection module 285.

Figure 3A:
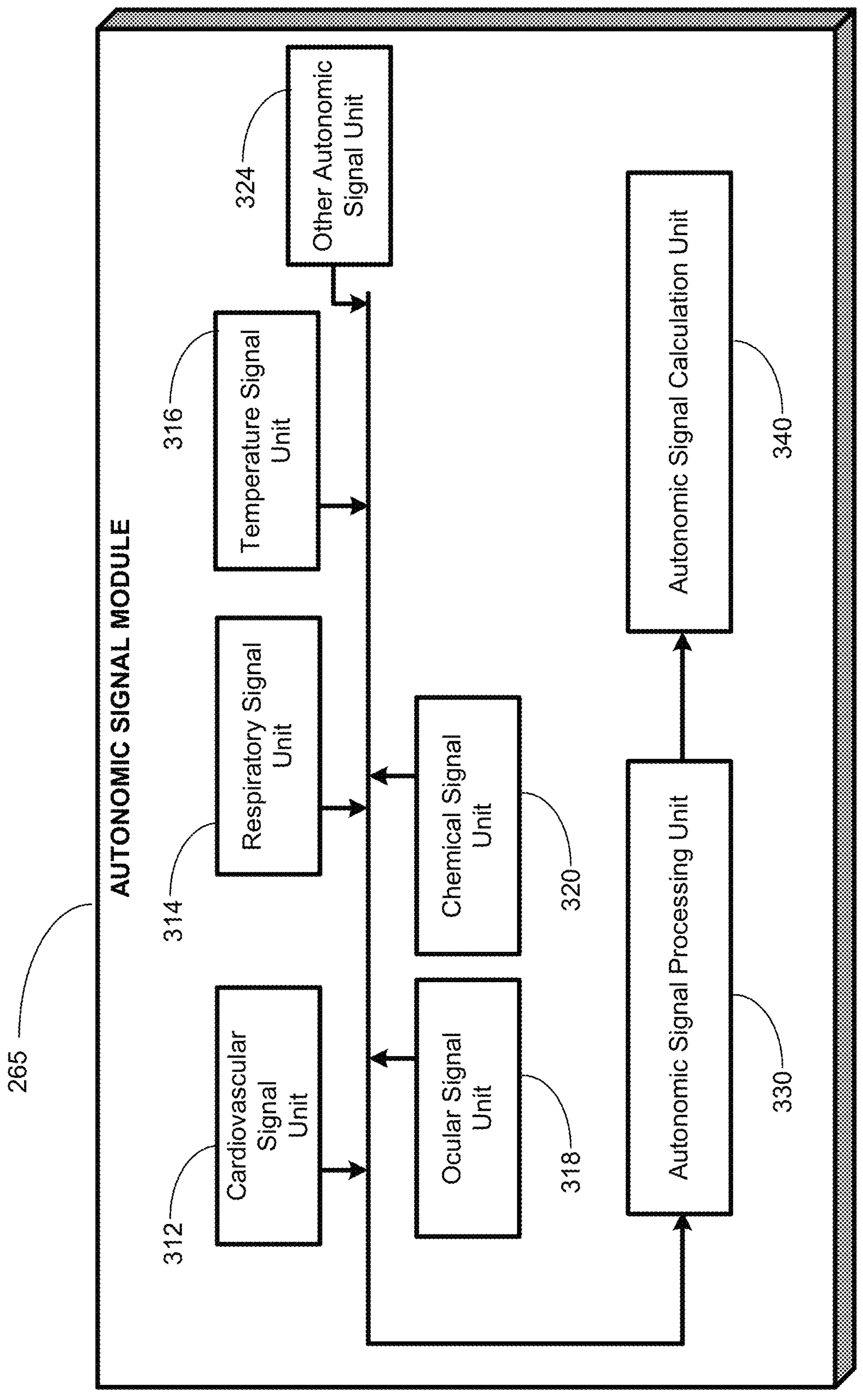
FIG. 3A provides a block diagram of a cardiac signal module of a medical device, in accordance with one illustrative embodiment of the present invention.
Figure 3B:
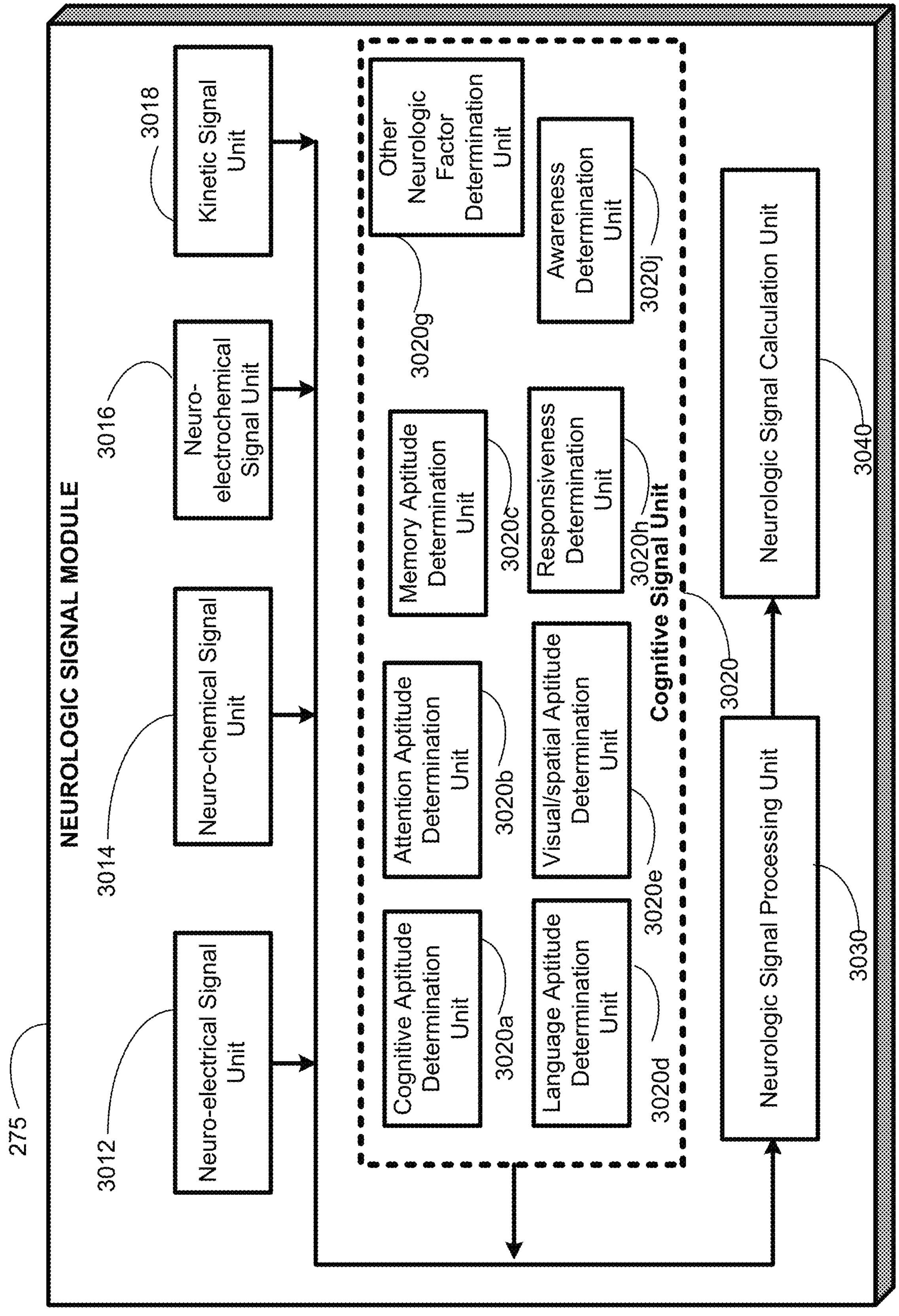
FIG. 3B provides a block diagram of a kinetic signal module of a medical device, in accordance with one illustrative embodiment of the present invention.

FIG. 3A and FIG. 3B are generally as shown and described in U.S. patent application Ser. No. 12/896,525, filed Oct. 1, 2010. The ocular signal unit 318 is generally capable of providing at least one ocular signal (e.g., pupil dilation, pupillary hippus, blinking, etc.).

FIG. 3B herein also depicts an awareness determination unit 3020*j*.

In addition, a device can comprise other signal modules. For example, it may comprise a metabolic signal module, which can comprise a blood parameter signal unit capable of providing at least one blood parameter signal (e.g., blood glucose, blood pH, blood gas, etc). Alternatively or in addition, the metabolic signal module can comprise a hormone signal unit capable of providing at least one hormone signal.

Figure 3C:
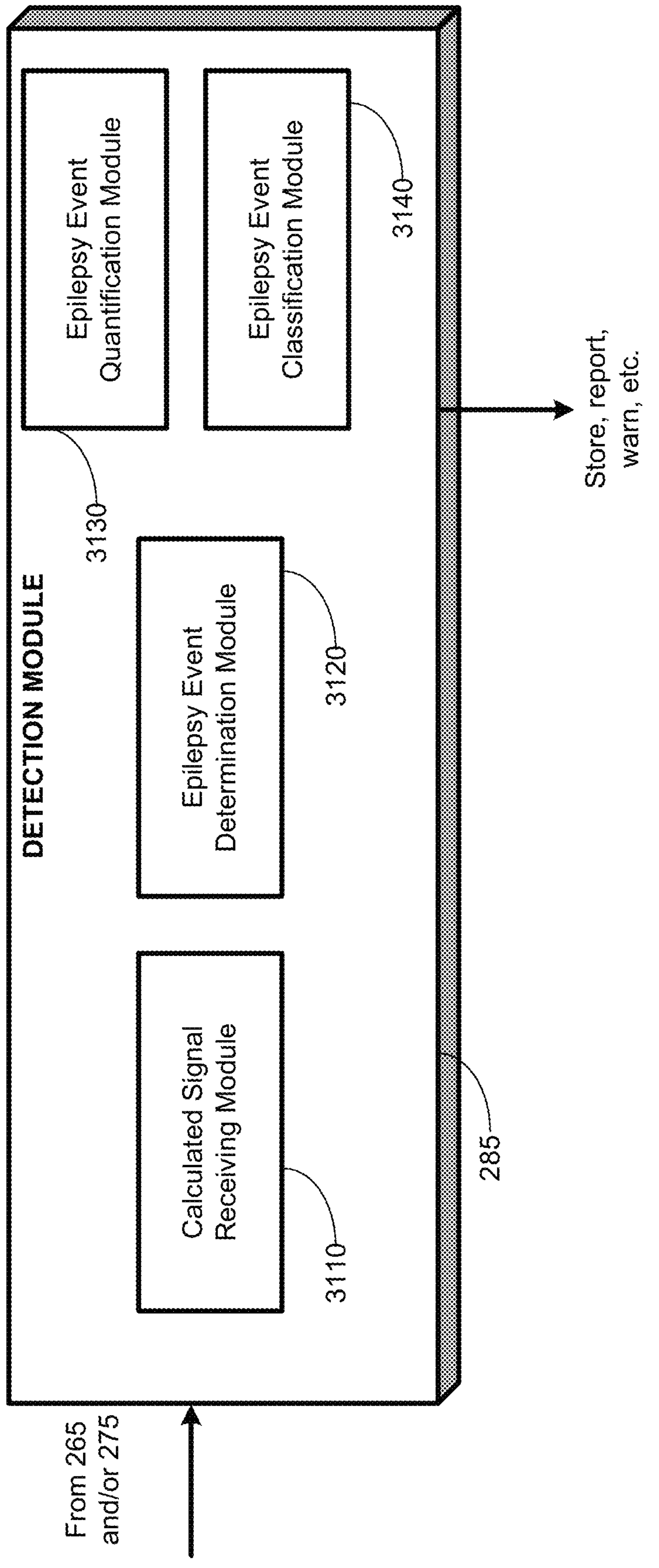
FIG. 3C provides a block diagram of a detection module of a medical device, in accordance with one illustrative embodiment of the present invention.
Figure 4:
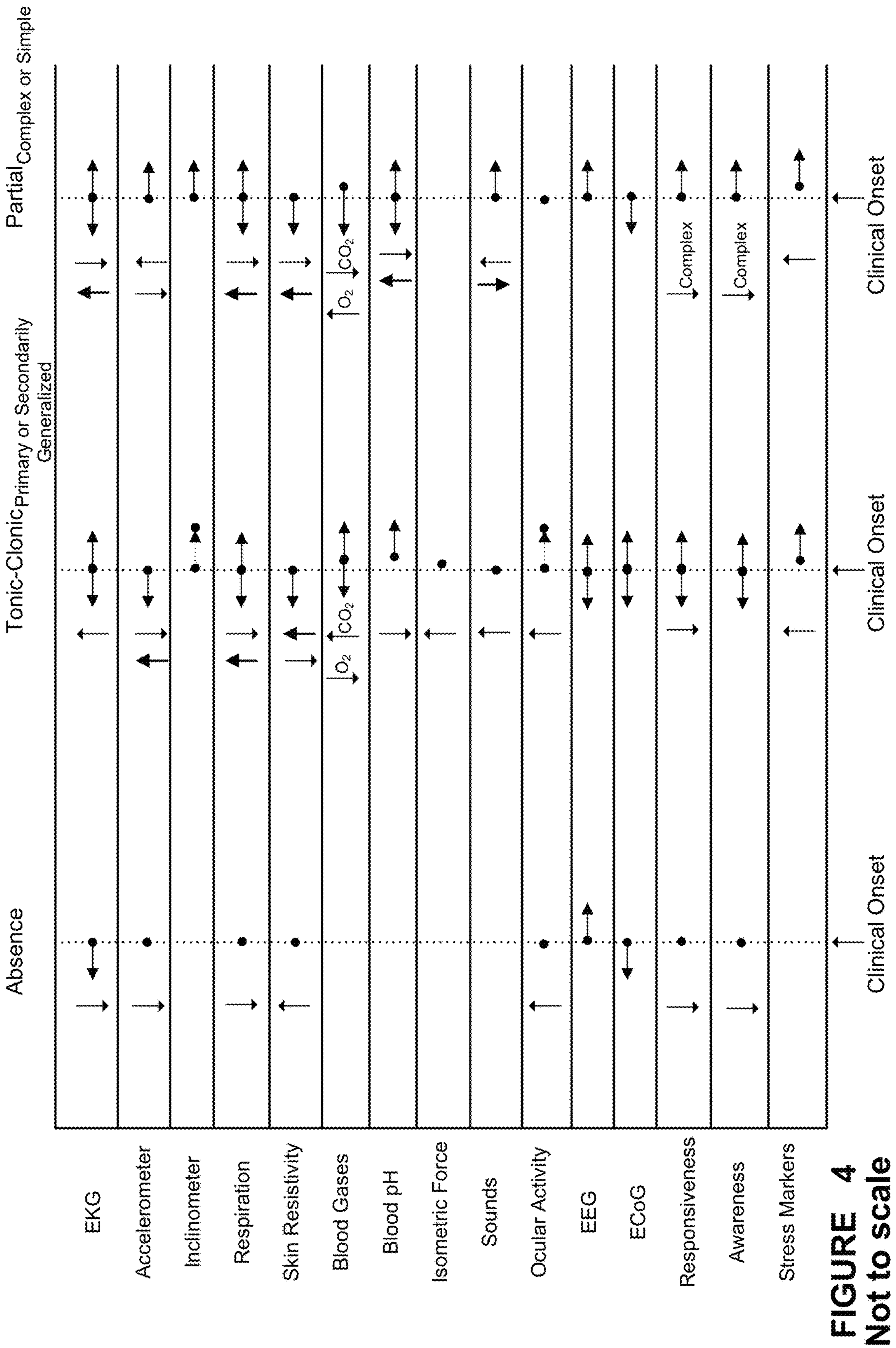
FIG. 4 shows the time of appearance (relative to clinical onset, dashed vertical line) and direction of deviations from reference activity of a plurality of body signals for four seizure types, specifically, absence seizures, tonic-clonic seizures, and simple or complex partial seizures.
Figure 5:
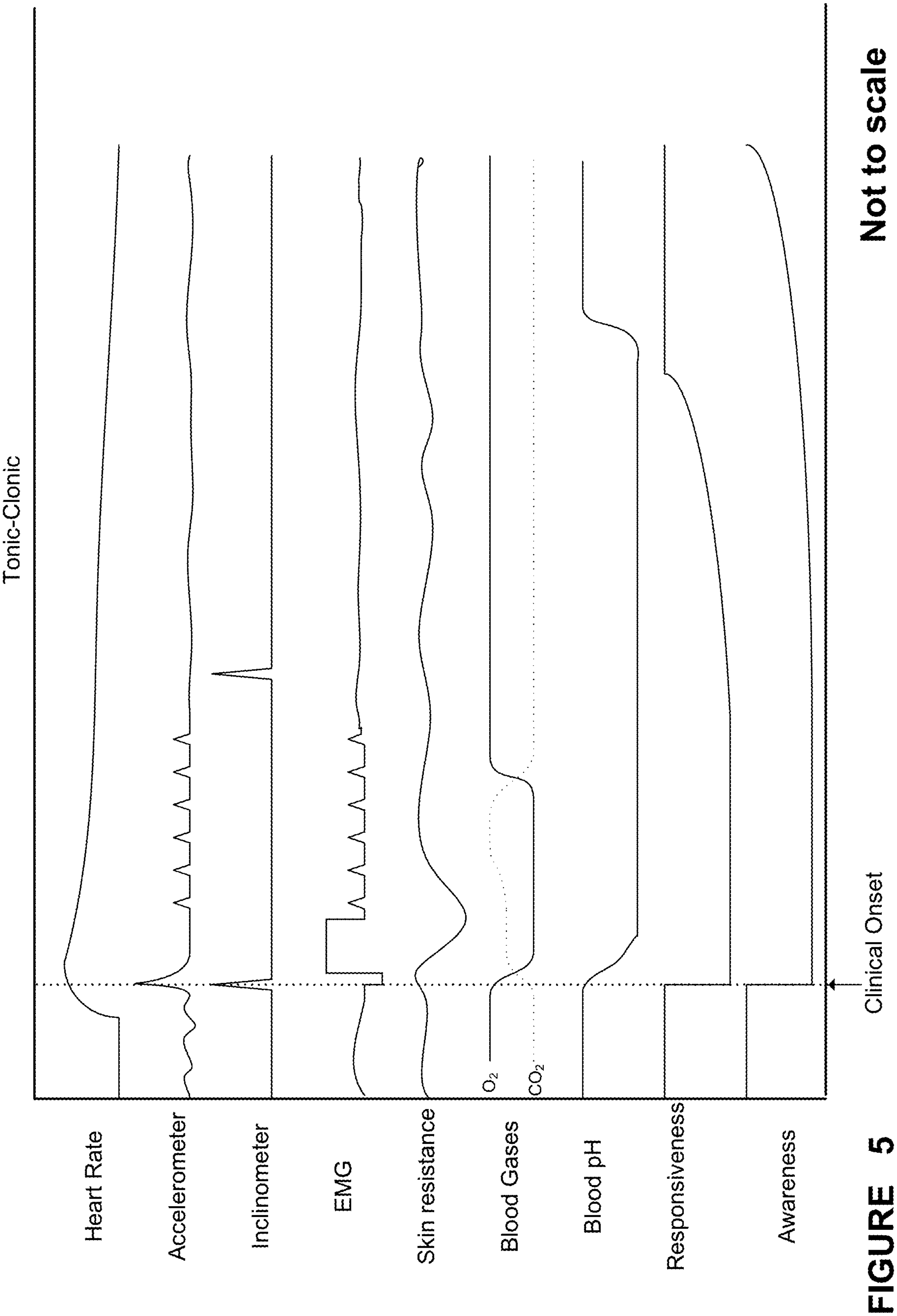
FIG. 5 shows time courses (relative to clinical onset, dashed vertical line) of activity of a plurality of body signals for tonic-clonic seizures.
Figure 6:
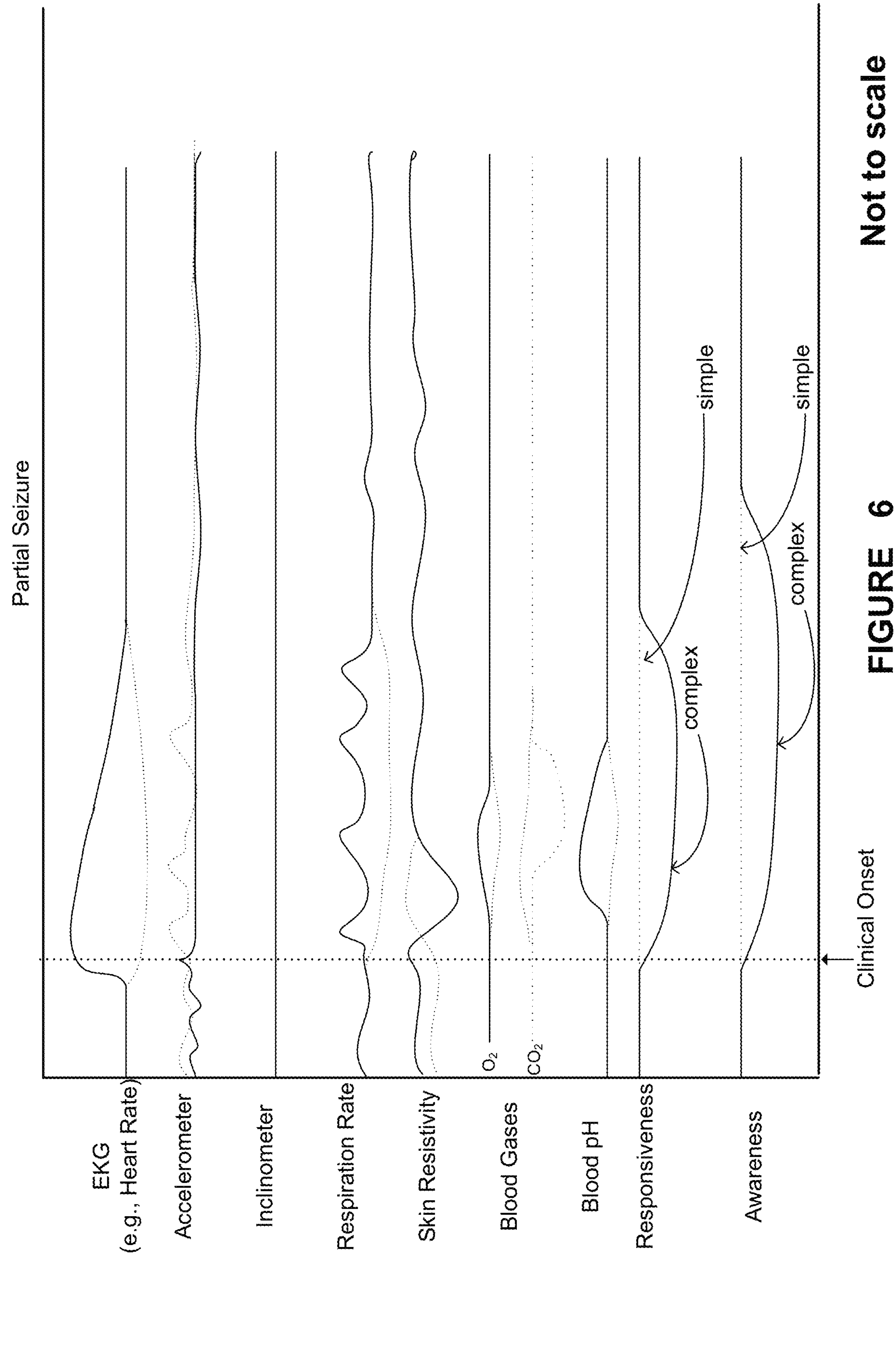
FIG. 6 shows time courses (relative to clinical onset, dashed vertical line) of activity of a plurality of body signals for partial (simple or complex) seizures.
Figure 7:
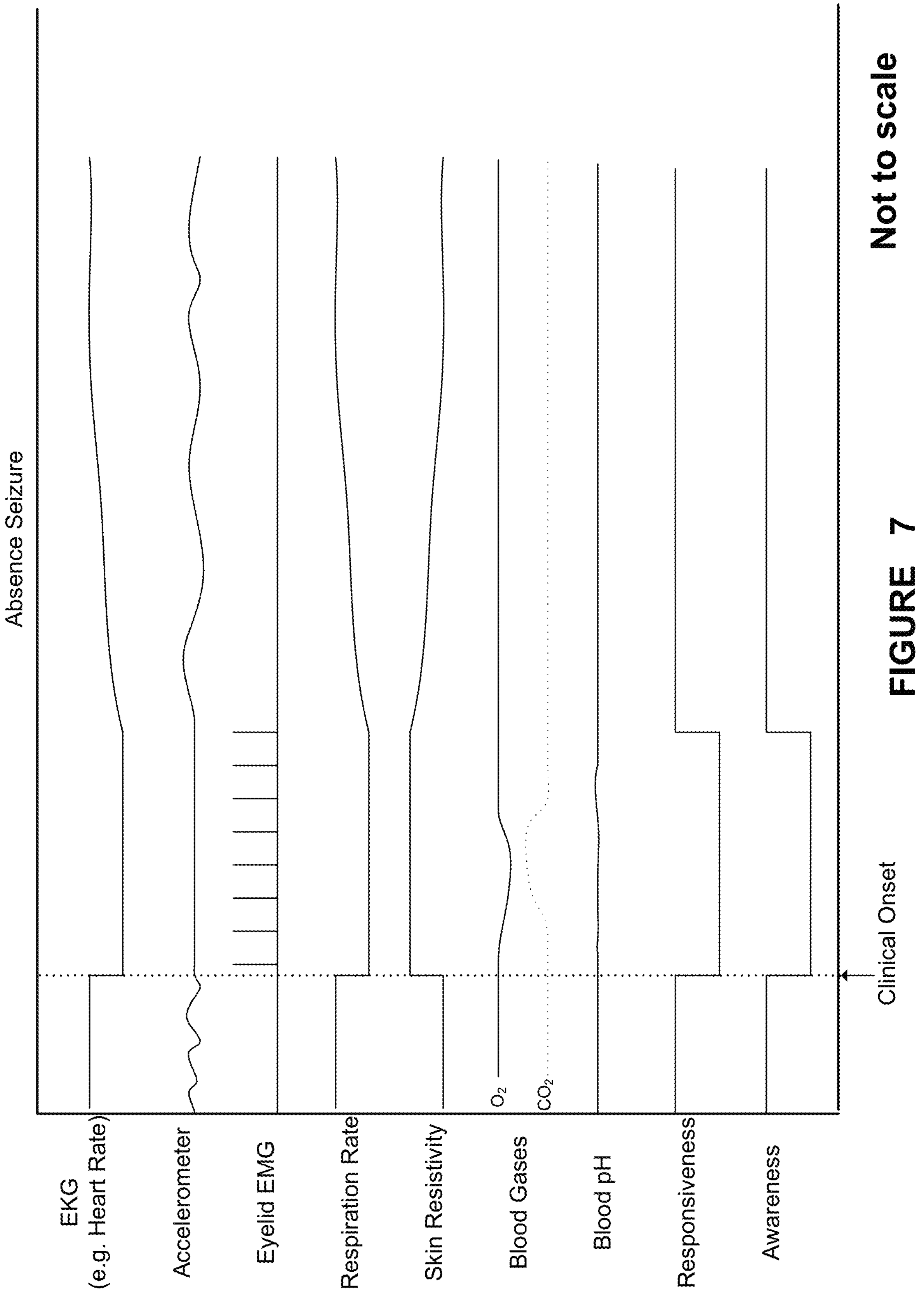
FIG. 7 shows time courses (relative to clinical onset, dashed vertical line) of activity of a plurality of body signals for idiopathic absence seizures.
Figure 8:
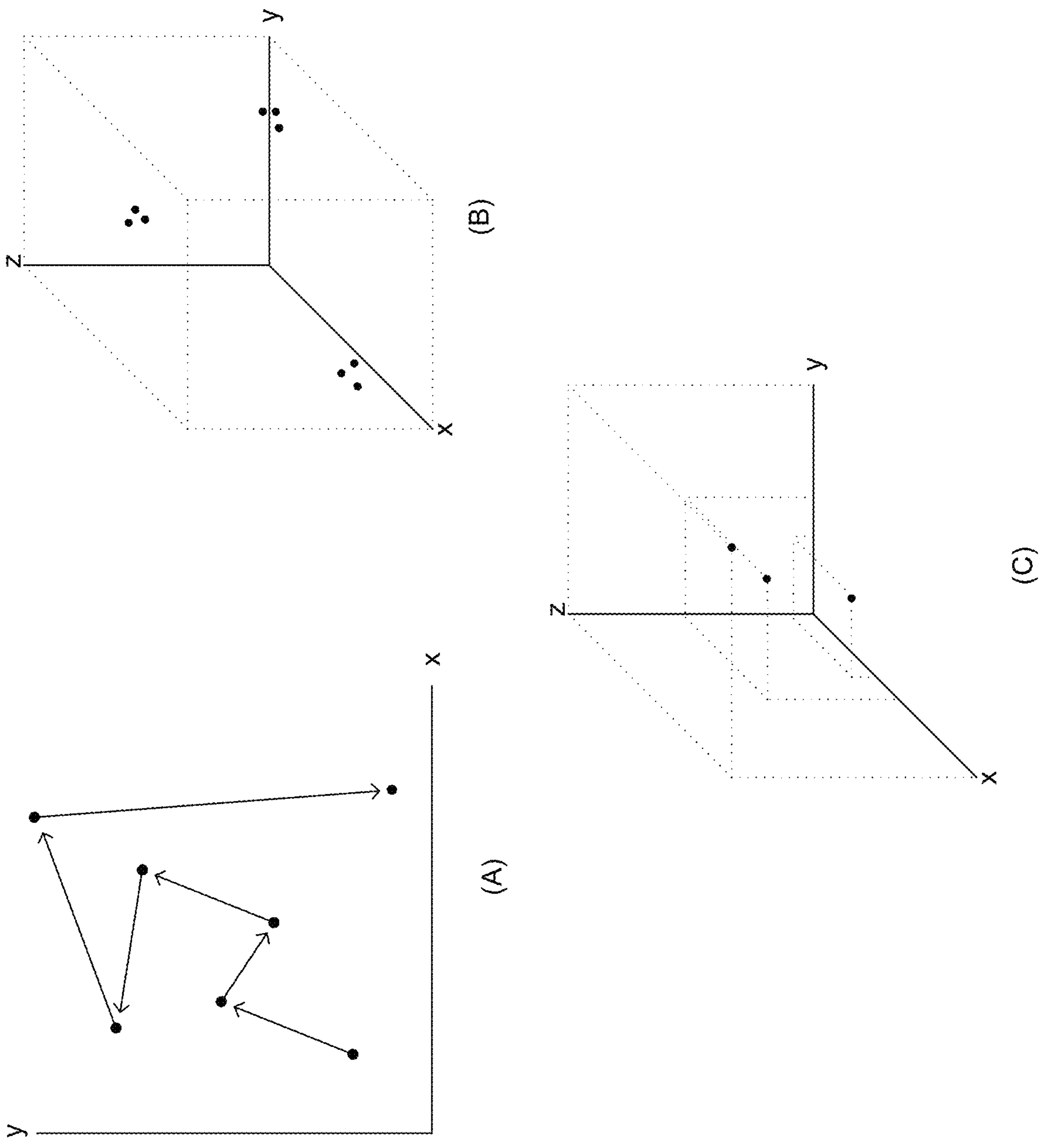
FIG. 8 shows (A) an exemplary two-dimensional plot of a trajectory of epileptic movements, (B) an exemplary three-dimensional plot of epileptic movements, and (C) an additional exemplary three-dimensional plot of epileptic movements.
Figure 9:
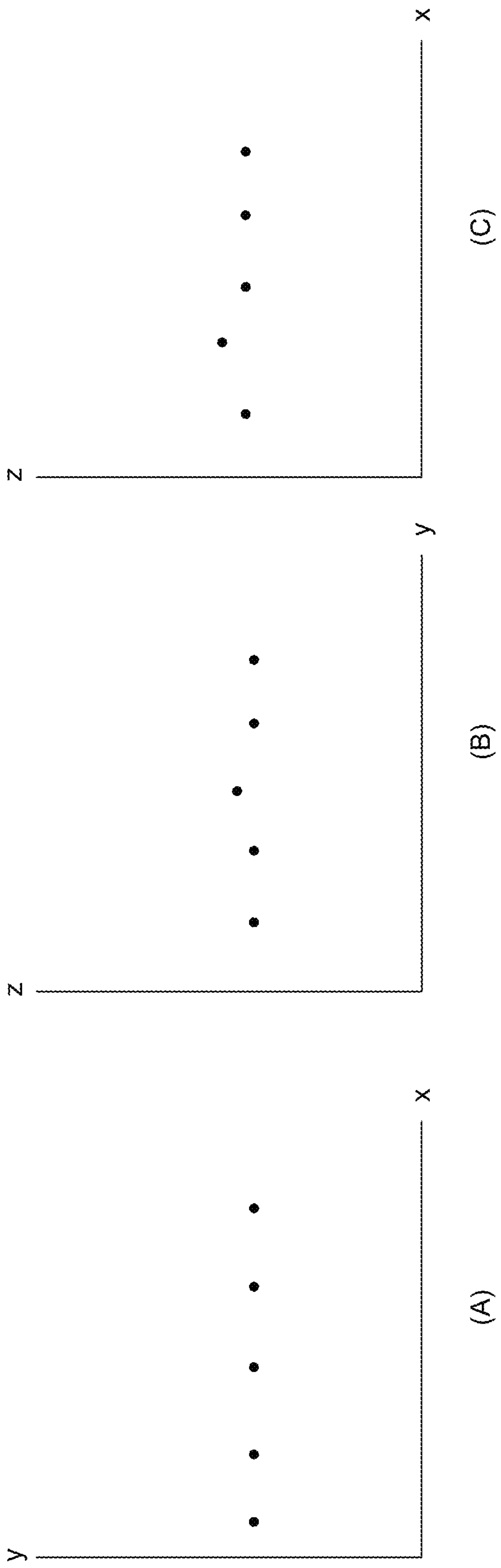
FIG. 9 shows three two-dimensional, temporally cumulative plots of discrete movements during the clonic phase of a primarily or secondarily generalized tonic-clonic seizure.

A detection module 285, as shown in FIG. 3C, is generally described in U.S. patent application Ser. No. 12/896,525, filed Oct. 1, 2010.

The above methods may be performed by a computer readable program storage device encoded with instructions that, when executed by a computer, perform the method described herein.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

What is claimed:

1. A method for detecting an epileptic event, comprising:

obtaining via one or more processors a cardiac signal indicative of a patient's heart beats;

obtaining via the one or more processors a kinetic signal indicative of a body movement of the patient;

detecting an indication of an epileptic event via the one or more processors based on the cardiac signal and the kinetic signal;

initiating to the patient via the one or more processors a test of the patient's responsiveness based on the indication of the epileptic event; and initiating via the one or more processors a therapy based on the test of the patient's responsiveness result.

2. The method of claim 1, wherein the detection is based on changes in the cardiac signal, changes in the kinetic signal, or both.

3. The method of claim 1, wherein the detection of the epileptic event further comprises detecting a potential epileptic event based on the cardiac signal and confirming the potential epileptic event as the epileptic event based on the kinetic signal.

4. The method of claim 1, wherein the detection of the epileptic event further comprises detecting a potential epileptic event based on the kinetic signal and confirming the potential epileptic event as the epileptic event based on the cardiac signal.

5. The method of claim 1, wherein the detecting further comprises determining at least one cardiac parameter from the cardiac signal, characterizing the cardiac parameter as either indicative of an epileptic seizure or not indicative of the epileptic seizure, determining at least one kinetic parameter from the kinetic signal, characterizing the kinetic parameter as either indicative of the epileptic seizure or not indicative of the epileptic seizure, and determining the occurrence of the epileptic event based on both the cardiac parameter and the kinetic parameter being indicative of the epileptic seizure.

6. The method of claim 1, further comprising classifying the epileptic event based on the cardiac signal, the kinetic signal, or both.

7. The method of claim 1, wherein the cardiac signal is obtained from an electrocardiogram.

8. The method of claim 1, wherein the kinetic signal is obtained from an accelerometer, an inclinometer, an actigraph, or two or more thereof.

9. The method of claim 1, further comprising obtaining via the one or more processors a responsiveness signal indicative of a patient's responsiveness and characterizing the epileptic event based on the responsiveness signal.

10. The method of claim 1, further comprising obtaining via the one or more processors an awareness signal indicative of a patient's awareness and characterizing the epileptic event based on the awareness signal.

11. The method of claim 1, wherein the detecting further comprises utilizing a temporal relationship between the cardiac signal and the kinetic signal in the detection procedure.

12. The method of claim 1, wherein the epileptic event is classified based on the test of the patient's responsiveness result.

* * * * *